(12) United States Patent
Murakami et al.

(10) Patent No.: US 9,242,117 B2
(45) Date of Patent: Jan. 26, 2016

(54) MAGNETIC INDUCTION SYSTEM AND OPERATING METHOD FOR SAME INCORPORATION BY REFERENCE

(75) Inventors: Masato Murakami, Tokyo (JP); Mitsuo Ochi, Hiroshima (JP)

(73) Assignees: SHIBAURA INSTITUTE OF TECHNOLOGY, Tokyo (JP); HIROSHIMA UNIVERSITY, Hiroshima (JP)

( * ) Notice: Subject to any disclaimer, the term of this patent is extended or adjusted under 35 U.S.C. 154(b) by 869 days.

(21) Appl. No.: 13/503,255

(22) PCT Filed: Oct. 25, 2010

(86) PCT No.: PCT/JP2010/068863
§ 371 (c)(1),
(2), (4) Date: Jul. 30, 2012

(87) PCT Pub. No.: WO2011/049236
PCT Pub. Date: Apr. 28, 2011

(65) Prior Publication Data
US 2012/0289764 A1    Nov. 15, 2012

(30) Foreign Application Priority Data

Oct. 23, 2009  (JP) ................................. 2009-244942

(51) Int. Cl.
*A61N 2/02*    (2006.01)
*A61N 2/00*    (2006.01)
(Continued)

(52) U.S. Cl.
CPC ........ *A61N 2/002* (2013.01); *H01F 6/00* (2013.01); *A61B 2019/2253* (2013.01); *A61N 2/02* (2013.01)

(58) Field of Classification Search
CPC ........... A61N 2/00; A61N 2/002; A61N 2/02; A61N 2/004; A61B 19/22; A61B 2019/2253; A61B 2019/2257; A61B 2019/2261; A61B 2019/2265

USPC ..................................................... 600/9–15
See application file for complete search history.

(56) References Cited

U.S. PATENT DOCUMENTS 5,078,140 A * 1/1992 Kwoh .......................... 600/417
5,278,137 A * 1/1994 Morita et al. ................. 505/125
(Continued)

FOREIGN PATENT DOCUMENTS

JP    2001-358007 A    12/2001
JP    2007-151605 A     6/2007
(Continued)

OTHER PUBLICATIONS

International Preliminary Report on Patentability, Forms PCT/IB/338 and PCT/IPEA/409 (English translation attached) for PCT/JP2010/068863.
(Continued)

*Primary Examiner* — Charles A Marmor, II
*Assistant Examiner* — Carrie R Dorna
(74) *Attorney, Agent, or Firm* — Birch, Stewart, Kolasch & Birch, LLP

(57) ABSTRACT

The invention provides a magnetic induction system and an operating method for it in which the magnetic force can be made to act deeply and widely in any desired direction. The magnetic induction system of the invention contains multiple magnetic field generation means formed of a superconductive bulk magnet, a drive means for arranging the magnetic field generation means at a desired site and angle, and a drive control means for driving the driving means and controlling the position and the angle of the multiple magnetic field generation means so that a magnetic complex can be inducted to the desired position in a body by the synthetic magnetic field formed by the multiple magnetic field generation means, whereby the magnetic complex is inducted to be concentrated in the cartilage defected part.

18 Claims, 16 Drawing Sheets

(51) Int. Cl.
*H01F 6/00* (2006.01)
*A61B 19/00* (2006.01)

(56) References Cited

U.S. PATENT DOCUMENTS

| | | | |
|---|---|---|---|
| 6,157,853 A * | 12/2000 | Blume et al. | 600/426 |
| 2002/0022777 A1 | 2/2002 | Crieghton, IV et al. | |
| 2005/0204748 A1* | 9/2005 | Yamanaka et al. | 62/3.7 |
| 2006/0264690 A1 | 11/2006 | Ochi | |
| 2009/0287036 A1* | 11/2009 | Shapiro et al. | 600/12 |
| 2011/0144411 A1* | 6/2011 | Sandhu et al. | 600/13 |

FOREIGN PATENT DOCUMENTS

| | | |
|---|---|---|
| JP | 2007-297290 A | 11/2007 |
| WO | WO 2006/035550 A1 | 4/2006 |
| WO | 2006-325600 A | 12/2006 |
| WO | WO 2009/086071 A2 | 7/2009 |

OTHER PUBLICATIONS

International Search Report issued in PCT/JP2010/068863 dated Nov. 22, 2010.

Japanese Notice of Allowance dated Dec. 22, 2014, for Japanese Application No. 2011-537331.

* cited by examiner

MAGNETIC INDUCTION SYSTEM AND OPERATING METHOD FOR SAME INCORPORATION BY REFERENCE

INCORPORATION BY REFERENCE

The present application claims priority to Japanese Patent Application No. 2009-244942, filed Oct. 23, 2009, the content of which is incorporated in the present application by reference.

TECHNICAL FIELD

The present invention relates to a magnetic induction system and an operating method for a magnetic induction system, in which an inductee provided with magnetic particles is inducted.

BACKGROUND ART

For example, exfoliative osteochondritis, which is a disease of such that the cartilage of a joint falls out from the bone of the lower layer together with a thin bone fragments, as caused by the blood circulation failure in the bone or the cartilage of a knee joint triggered by injury or sporting activity, much occurs on the inside of a knee, and is seen in teenage children whose osteochondral bonding force during development is weak; and the patients with the disease first complain knee pain and swelling, and their pain worsens in walking or exercise; and when the bone or the cartilage exfoliates in development of the disease, then the knee may feel discomfort when bent or stretched or would fail to bend or stretch. The cartilage does not have a blood vessel and a nerve tissue, and when damaged, the cartilage could not become normal again naturally. Heretofore, there have been employed a method of intentionally damaging the bone in the depth of the damaged part by drilling for bleeding to expect the regeneration of the tissue, and a method of implanting multiple small cartilages so as to fill up the defect, by which, however, an extremely smooth condition intrinsic to joints could not be reproduced.

One example of a conventional medical treatment for regenerative medicine for cartilage injury, capable of reproducing an extremely smooth condition intrinsic to joints, comprises collecting the cartilage tissue of the part of a joint of a patient to which the body weight is not given, in a size of from 5 to 10 mm square using an endoscope, decomposing the tissue with an enzyme to take out the cells from the body, winding them around a medical collagen gel of which the shape is so controlled as to correspond to the shape of the defect, adding the patient's serum thereto, and cultivating it for about 3 weeks. This is fitted in the defect by surgery, then covered with the patient's periosteum and stitched up. In one month to one and a half months, the patient can walk with placing all of his (her) body weight on the surgery site. According to the method, when the surgery site is covered with the patient's periosteum and stitched up, the patient's knee part must be cut and opened to a range of a few tens mm square, which is problematic in that the physical load to be given to the patient is large.

As a conventional therapeutical method capable of reducing the physical load to patient, for example, development of regenerative medicine technology has been promoted, which comprises preparing a complex of cells for medical treatment such as bone marrow mesenchymal stem cells or the like and magnetic particles, injecting the complex into the area around the affected part in the body of a patient with a syringe or the like, applying a magnetic force thereto from outside the body to thereby focus the complex in the affected part so as to cure the injury of the part.

As a magnetic induction apparatus for magnetically inducting an inductee provided with conventional magnetic particles used for disorders such as cartilage injury or the like, by utilizing the magnetic field generated by a magnetic field generator, there has been proposed a structure where a doughnut-shaped solenoid coil magnet is sued and the solenoid coil magnet is arranged to surround the affected part of a patient (for example, see Patent Reference 1).

On the other hand, development of regenerative medicine technology has been promoted, which comprises arranging a permanent magnet outside the body of a patient and around the affected part inside the body of the patient, applying a magnetic force thereto in an arbitrary direction, injecting a complex of cells for use for the medical treatment and magnetic particles into the body by the use of a syringe, and focusing the complex in the affected part in which the complex is desired to be focused, thereby curing the injury (for example, see Patent Reference 2).

On the other hand, for example, there has been proposed a method where a complex magnetic medicine formed by bonding a curative medicine to magnetic particles is administered into the blood vessel of a patient with a syringe or the like, a magnetic field generator formed of a superconductive bulk magnet is arranged around the bed on which the patient lies, the magnet is addressed to the area around the blood vessel branching part upstream the cancer cells of the patient and around the cancer cells, the magnetic medicine occasionally running through the magnetic field along the blood flow circulating in the body of the patient is captured by the magnetic force so as to increase the residual density of the magnetic medicine around the affected part (for example, see Patent Reference 3).

CITATION LIST

Patent References

Patent Reference 1: JP-A 2007-151605
Patent Reference 2: JP-A 2006-325600
Patent Reference 3: JP-A 2007-297290

SUMMARY OF THE INVENTION

Problems That the Invention is to Solve

In the conventional magnetic induction apparatus where the magnetic generator for generating the magnetic field necessary for magnetically inducting the inductee injected from outside into the body of a patient is a solenoid coil magnet, the solenoid coil magnet generates a strong magnetic field around the periphery of the coil and such a strong magnetic field is thereby generated like a ring. Accordingly, in case where the leg of a patient is made to run through the center space part of the solenoid coil magnet and is so arranged that the inside of the knee is kept in contact with the peripheral edge of the coil circle, the line of magnetic action acts linearly toward the center of the magnet in the circular cross section of the magnet from the radial direction thereof. Accordingly, in case where the route to connect the site inside the body in which the inductee is injected by the use of, for example, a syringe and the affected part in which the inductee is desired to be focused does not correspond to the line of magnetic action, or that is, when there is a defect in the side part of the knee of which the plane where the inductee is desired to be focused is parallel to the circular cross section or in the articular cartilage in the plane at an angle of, for example, 45 degrees to the circular cross section, there occurs a problem in that the inductee could not be focused in the affected part.

In another case, the body itself of a patient may be an obstacle, and there may occur another problem in that the magnetic line could not be suitably applied to the affected part.

In case where the magnetic field generator is a permanent magnet, the magnetic force of the permanent magnet drastically attenuates as separating from the surface of the magnet, and therefore when the affected part is separated by 5 cm from the place where the permanent magnet is installed, there is a problem in that the inductee could hardly be focused in the affected part.

On the other hand, in case where a complex of a curative medicine bonded to magnetic particles, for example, a complex magnetic medicine that comprises a complex of cells for medical treatment such as bone marrow mesenchymal stem cells or the like and magnetic particles is administered into the blood vessel of a patient with a syringe or the like, and the magnetic medicine is inducted by using a magnetic field generator formed of a superconductive bulk magnet, there is a problem in that the magnetic medicine could not be magnetically inducted to the cartilage-injured affected part or the like with no blood vessel running therethrough.

The present invention has been made in consideration of the problems as above, and an object of the invention is to provide a magnetic induction system capable of inducting an inductee to the desired site in a subject.

Another object of the invention is to provide a magnetic induction system which, even in a case where the body itself of a patient is an obstacle or even in a complicated site such as the inside of a knee or in an narrow site, can provide a suitable magnetic force anywhere so as to induct the inductee in the desired position inside the body of a subject and which can be readily moved and can be installed in an narrower space than usual.

Means for Solving the Problems (1. Magnetic Induction System)
(First Embodiment)

For attaining the above-mentioned objects, there is provided the magnetic induction system of the invention. The magnetic induction system of the first embodiment of the invention comprises multiple probe-like magnetic field generation means, a computing means for computing the position and the angle of the magnetic field generation means in order that the synthetic magnetic field formed by the multiple magnetic field generation means could act on the desired site in a living body, and a drive control means for controlling a drive means so that the multiple magnetic field generation means could be in the position and at the angle computed by the computing means.

The "magnetic field generation means" has a probe-like form and is preferably provided with a superconductive bulk magnet unit. The magnetic field generation end part of the magnetic field generation means is so arranged that the position and the direction thereof could be controlled in any desired manner near the body surface of a living body. Near the body surface, the part can be moved along the body surface, and can be appropriately used in accordance with the form and the posture of the body. For example, the part can be moved and stopped at any narrow position such as the back or the side of a knee, etc., and can be so arranged that the magnetic field lines could act deeply anywhere in the body at any desired angle to the affected part of a patient. The multiple "magnetic field generation means" can magnetically induct the magnetic complex in any desired direction by changing the intensity and the direction of the magnetic field from each magnetic field generation means so as to change the direction and the intensity of the resultant magnetic force vector.

The magnetic field generation means may be so designed as to be equipped with a "superconductive bulk magnet" for generating a magnetic field. The magnetic field generation face of the superconductive bulk magnet can generate a strong magnetic force of from several tens times to several hundreds times as compared with a permanent magnet having the same size, and therefore can favorably induct the complex that has been injected into the area outside the blood vessel and around the affected part in the body, using a syringe or the like, in the cartilage defected part in which the complex is desired to be focused. The superconductive bulk magnet is small and light, and is therefore suitable for use in the magnetic induction system of the present invention that can be installed even in a narrow place.

Regarding the composition of the superconductive bulk magnet, preferred is a bulk magnet capable of providing a high critical current density of 10000 A/cm$^2$ and capable of providing a sufficient trapping magnetic field at a liquid nitrogen temperature of not lower than 77K and, for example, in a magnetic field of 3 T. For example, preferred is a bulk magnet having a composition of RE—Ba—Cu—O (RE: rare earth element). Concretely, more preferred is (Nd, Eu, Gd)—Ba—Cu—O, Gd—Ba—Cu—O or Y—Ba—Cu—O.

For enhancing the thermal conductivity, an aluminium rod may be inserted into the hole formed in the superconductive bulk magnet to give a complex magnet, or a shape-memory alloy-made ring may be fitted to the magnet. Also if desired, a resin or a low-melting-point alloy such as wood metal or the like may be infiltrated into the superconductive bulk magnet to thereby enhance the mechanical strength of the resulting magnet for use herein. Usable here are the superconductive bulk magnets modified by employing all the above-mentioned constitution of inserting an aluminium rod to form a complex magnet, the constitution of fitting a shape-memory alloy-made ring and the constitution of infiltrating with a low-melting-point alloy.

The "drive means" can drive the multiple magnetic field generation means. In this, "multiple" means two or three or more, but is preferably two from the viewpoint of easy controllability. The drive means supports the magnetic field generation means and has the function capable of arranging the magnetic field generation end part in any desired position and in any desired direction near the body surface of a living body. Owing to the drive means having the function, the magnetic field generation means can be so controlled that the magnetic force can deeply act inside the body at any desired angle to the affected part of the patient, not moving the patient. For the drive means, usable is an ordinary drive motor or the like, and for this, a constitution comprising "magnet holder", "arm", "rotary joint part", "carriage" and others may be taken into consideration. By the carriage, a bed may be moved to the predetermined position, and further by the arm and the rotary joint part, the position of the magnetic field generation means can be adjusted. By the drive means, the superconductive bulk magnet can be moved and stopped in any desired narrow place such as the back or the side of a knee or the like, or the movement thereof can be continuously regulated.

The "computing means" can compute the position and the angle of the magnetic field generation means so that the synthetic magnetic field can be inducted to the desired site in the body. The computing means is composed of CPU, main memory, RAM, etc.

In the memory of the computing means, the relationship between the position and the angle of the magnetic field generation means previously defined on the basis of experiments and others, and the synthetic magnetic field to be formed at the position and at the angle of the magnetic field generation means is mapped, and may be so designed as to be stored in a table or a map. The computing means can compute the position and the angle of the magnetic field generation means with reference to the data mapped inside the memory.

Using the function previously stored in the memory of the computing means, the position and the angle of the magnetic field generation means may be automatically computed. The computing means can compute the position and the angle of the magnetic field generation means by inputting the data of the desired position at which a synthetic magnetic field is to be generated, in the function stored in the memory.

The "drive control means" has the function capable of controlling the control means so that a magnetic bead-inductee complex can be inducted to the desired position in a body by the action of the synthetic magnetic field formed by the multiple magnetic field generation means. The above-mentioned computing means computes the position and the angle of the magnetic field generation means so that the multiple magnetic field generation means can form a synthetic magnetic field in the desired site of a body, and the drive control means control the drive means so that the multiple magnetic field generation means can be in the position and at the angle computed by the computing means. As the controlling method, control via a wireless signal or a wire cable may be taken into consideration.

The desired site in a body in which the synthetic magnetic field is formed is, for example, the joint cartilage part in a body. The desired site is the affected part or the part to be examined of a patient, and for example, the site may be a cartilage defect part in which a defect exists. In this, the site in which the magnetic complex can be inducted in the magnetic induction system is not limited to the cartilage defect part but any other site in the body of a patient, such as a specific internal organ thereof or the like may be taken into consideration. For example, a suitable magnetic force can be act on a specific narrow site such as the cartilage defect part in a knee joint or the like, or on any other complicated site or narrow site such as the inside of a knee or the like, and a magnetic complex can be thereby inducted to the affected part. The route for magnetic complex induction is not limited to the part where a blood vessel or a nerve exists, but may be settled even in a cartilage part where a blood vessel or a nerve does not exist.

In the magnetic induction system of the invention, an "injection unit" having the function of injecting a magnetic bead-inductee complex into a body may be separately provided. As the injection unit, employable here is an ordinary syringe. The injection unit is not always integrated with the magnetic induction system, but may be a separate unit.

The "magnetic complex" is, for example, a magnetic bead-inductee complex that comprises a magnetic bead of a magnetic material and an inductee substance. The "magnetic bead-inductee complex" is characterized by containing a magnetic material to be formed for the purpose of being inducted to the desired site in a body by a magnetic induction apparatus. One example of the method for forming the magnetic bead-inductee complex that may be employable here comprises taking the mesenchymal stem cells of a patient that may change into the bone, the cartilage, the muscle or the like of the patient, out of the body of the patient, using magnetite fine particles for use as a contrast material or the like, coating the surfaces of the fine particles with, for example, a peptide or the like, and mixing the two in a liquid for a predetermined period of time thereby forming a complex of the stem cell and the magnetite fine particle bonding to each other via the peptide.

In the magnetic induction system of the invention, a case of using a magnetic complex formed of the cells to be used for medical treatment and magnetic particles is described in the above; however, not limited thereto, any magnetic complex is usable here that comprises magnetic particles and a biologic effective substance such as anticancer agent or the like having a therapeutical effect for the affected part. The magnetic induction system of the invention can be used not only for medical treatment for the affected part but also for clinical examination or diagnosis of the body of a subject. For example, using the magnetic induction system of the invention, the magnetic complex for clinical examination or diagnosis may be inducted to the site for examination or the site for diagnosis of the body of a subject.

(Second Embodiment)

The magnetic induction system of the second embodiment of the invention further comprises a like-pole control means capable of controlling the drive means at the position at which the magnetic poles of the multiple magnetic field generation means mutually repel each other at the desired site of a living body. The magnetic poles of the magnetic field generation ends of the individual multiple magnetic field generation means are like-poles.

The "like-pole control means" has the function capable of controlling the drive means at the position at which the magnetic fields generated by the multiple magnetic field generation means mutually repel each other in the magnetic field receiving region of a living body. The multiple magnetic field generation means generate homopolar magnetic fields from the magnetic field generation ends thereof, and the like-pole control means controls the drive means at the position at which the generated homopolar magnetic fields repel each other in the magnetic field receiving region of a living body. Having the "like-pole control means", the magnetic induction system of the invention is free from the risk of generating the power of tucking down the magnetic field receiving region (affected part) of a living body and therefore more safely facilitates the induction of magnetic bead-inductee complex.

The like-pole control means can favorably prevent a part of a body from being caught between the attracting heteropolar magnets and can prevent the body from being injured.

(Third Embodiment)

The magnetic induction system of the third embodiment of the invention further comprises a time control means of controlling the site in a living body and the intensity of the magnetic field at that site in accordance with the time elapsed after the introduction of magnetic complex.

The "time control means" has the function capable of controlling the intensity of the magnetic field in the magnetic field receiving region of the body in accordance with the time elapsed after the introduction of magnetic bead-inductee complex. For example, in case where a magnetic bead-inductee complex is introduced into a joint part, it may be considered that a relatively weak magnetic field is applied to that part in the initial stage in order that the introduced magnetic bead-inductee complex could be uniformly spread in the jelly-like body fluid in the joint part and the complex could be thereby uniformly distributed by the self dispersion thereof, and subsequently, a relatively strong magnetic field is made to act on that part whereby the complex could be uniformly implanted in the narrow site of the defected area of the joint part. Having the "time control means", the magnetic induction system of the invention enables the induction of magnetic bead-inductee complex in more diversified modes.
(Fourth Embodiment)

The magnetic complex induction system of the fourth embodiment of the invention is characterized by comprising a magnetic complex and the magnetic induction system of the invention, wherein the complex contains cells for medical treatment and magnetic particles, and the magnetic induction system is provided with a superconductive bulk magnet and a support means of moving and stopping the superconductive bulk magnet in a desired narrow site such as the back or the side of the knee of a subject, or continuously controlling the movement, and is so designed that the magnetic complex injected into the site except the blood vessel of the body of a patient can be inducted to the affected part of the patient by the magnetic field generated by the superconductive bulk magnet.

(2. Operating Method for Magnetic Induction System)

The invention also provides an operating method for a magnetic induction system that comprises multiple probe-like magnetic field generation means, a drive means for driving the multiple magnetic field generation means, a computing means for computing the position and the angle of the magnetic field generation means and a drive control means of controlling the drive means; the method comprising a step where the computing means computes the position and the angle of the magnetic field generation means in order that the synthetic magnetic field formed by the multiple magnetic field generation means could act on the desired site in a living body, and a step where the drive control means controls the drive means so that the multiple magnetic field generation means could be in the position and at the angle computed by the computing means.

Advantage of the Invention

The magnetic induction system of the invention uses a superconductive bulk magnet capable of generating a strong magnetic field as compared with conventional solenoid coil magnets or permanent magnets, in which, therefore, the magnetic force can act even on the site with no blood vessel running therethrough (for example, cartilage part) and even on the depth inside a body. Accordingly, the invention is advantageous in that, even in a case where the affected part exists in the site with no blood vessel running therethrough or in the depth inside a body, a magnetic complex can be inducted to the affected part.

In the magnetic induction system of the invention, multiple magnetic field generation means are sued and therefore a synthetic magnetic field can be formed in any desired direction, and consequently, a magnetic force can be sterically focused in any site in the body of a patient. In other words, the system can make a magnetic complex act on the affected part more appropriately to the site and the shape thereof.

According to the invention in which the position and the direction of the multiple magnetic field generation means are controlled, first the synthetic magnetic field can be made to act on a relatively broad range around the affected part in order that a magnetic complex is gradually inducted to the affected part, and next the range on which the synthetic magnetic field acts can be narrowed so that the magnetic complex can be inducted to the local area of the affected part. In that manner, by focusing the magnetic complex in the local area of the affected part, the magnetic complex can more effectively act on the affected part.

Further, using a small-size and lightweight superconductive bulk magnet, the invention provides a small-size and lightweight magnetic induction system, as compared with conventional magnetic induction systems using an ordinary solenoid coil magnet or permanent magnet. Accordingly, even in a case where the affected part exists in a narrow site such as the back or the side of a knee, the magnetic field generation means can be arranged at the desired site.

According to the magnetic induction system of the invention, a magnetic line can suitably act on the affected part of a patient even in a case where a part of the body of the patient is an obstacle. Further, the magnetic induction system of the invention is easier to move and can be installed in a narrower space than before, in which the magnetic force can be made to act deeply and widely in any desired direction.

In the magnetic induction system of the invention, the magnetic field generator may be formed of a small-size and lightweight superconductive bulk magnet, and the system can be used for inducting the complex formed of cells for medical treatment and magnetic particles, which is injected into a body using a syringe, in the affected part in which the complex is desired to be focused. The superconductive bulk magnet can generate a strong magnetic force of from several tens times to several hundreds times as compared with a permanent magnet having the same size, and therefore can induct the complex that has been injected around the affected part using a syringe or the like, favorably and at high density in the cartilage defected part in which the complex is desired to be focused.

In addition, the superconductive bulk magnet in the invention generates the main magnetic force in the direction perpendicular to the magnet face and, even in a space separated from the magnet face, the magnetic force is stronger than that from a conventional solenoid coil magnet or permanent magnet having the same size and can generate the main magnetic force in the direction perpendicular to the magnet face, and therefore, even when the affected part in which the complex is desired to be focused is at a position spaced by, for example, 5 cm from the magnet, the complex can be adequately inducted in the cartilage defected part.

As described above, the magnetic induction system of the invention uses a superconductive bulk magnet can generate the main magnetic force in the direction perpendicular to the magnet face, and even in a space separated from the magnet face, the system can generate the main magnetic force stronger than that from a conventional solenoid coil magnet or permanent magnet having the same size, in the direction perpendicular to the magnet face. Accordingly, even in a case where the affected part in which the complex is desired to be focused has a cartilage defected face at an angle of, for example, 45 degrees from the side of a knee, the magnet face can be moved and stopped by operating the moving and supporting means and can be thereby adequately arranged so that the magnetic force acting line that connects the cartilage defected face and the site in which the complex has been injected with a syringe or the like could well meet with the magnetic force line running from the magnet, not moving the patient. Consequently, the complex can be favorably and adequately inducted to the cartilage defected face.

The magnetic induction system of the invention uses a superconductive bulk magnet and therefore, even in a case where the cartilage defected face in which the complex is desired to be focused is at the bottom or the side having a recessed form, the position of the magnet can be well adjusted and installed not moving the patient, and consequently, the complex can be favorably and uniformly inducted onto the recessed area of the cartilage defected part. Concretely, while moved in the space outside the body and around the affected part, the magnet face may be continuously controlled so that the magnetic force acting line that connects the recessed face of the cartilage defected face having a recessed form and the site in which the complex has been injected with a syringe or the like could well meet with the line of magnetic force of the magnet.

The other objects, characteristics and advantage of the invention will be apparent from the description of the examples of the invention given below with reference to the drawings attached hereto.

MODE FOR CARRYING OUT THE INVENTION

Figure 1:
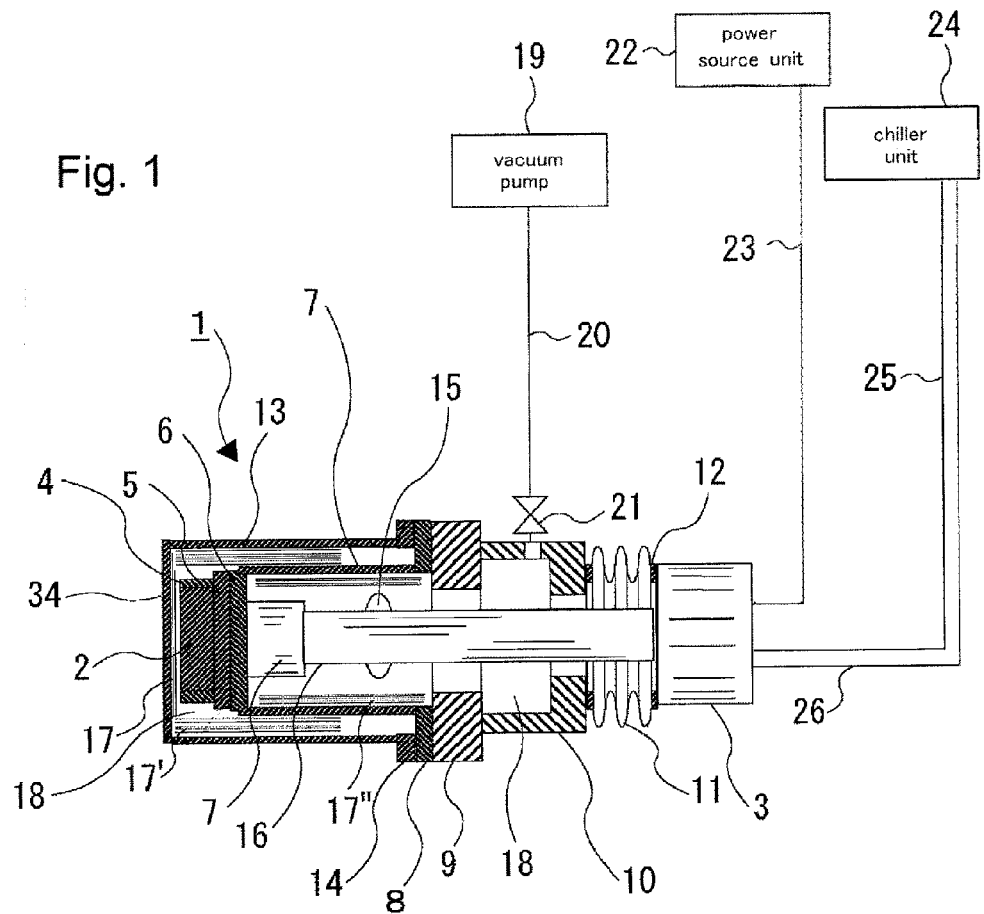
[FIG. 1] This is a view of illustrating the structure in the superconductive bulk magnet chamber of the magnetic inductions system of one example of the invention.
Figure 2:
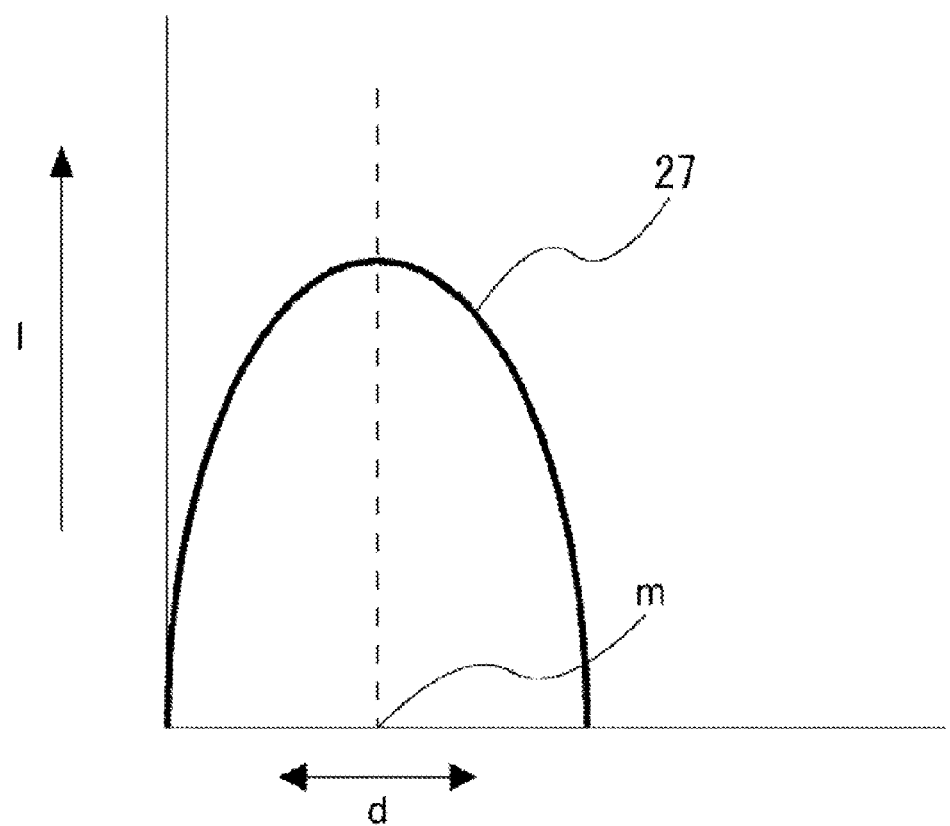
[FIG. 2] This is a view of generated magnetic field distribution on the superconductive bulk magnet surface in one example of the invention.
Figure 3:
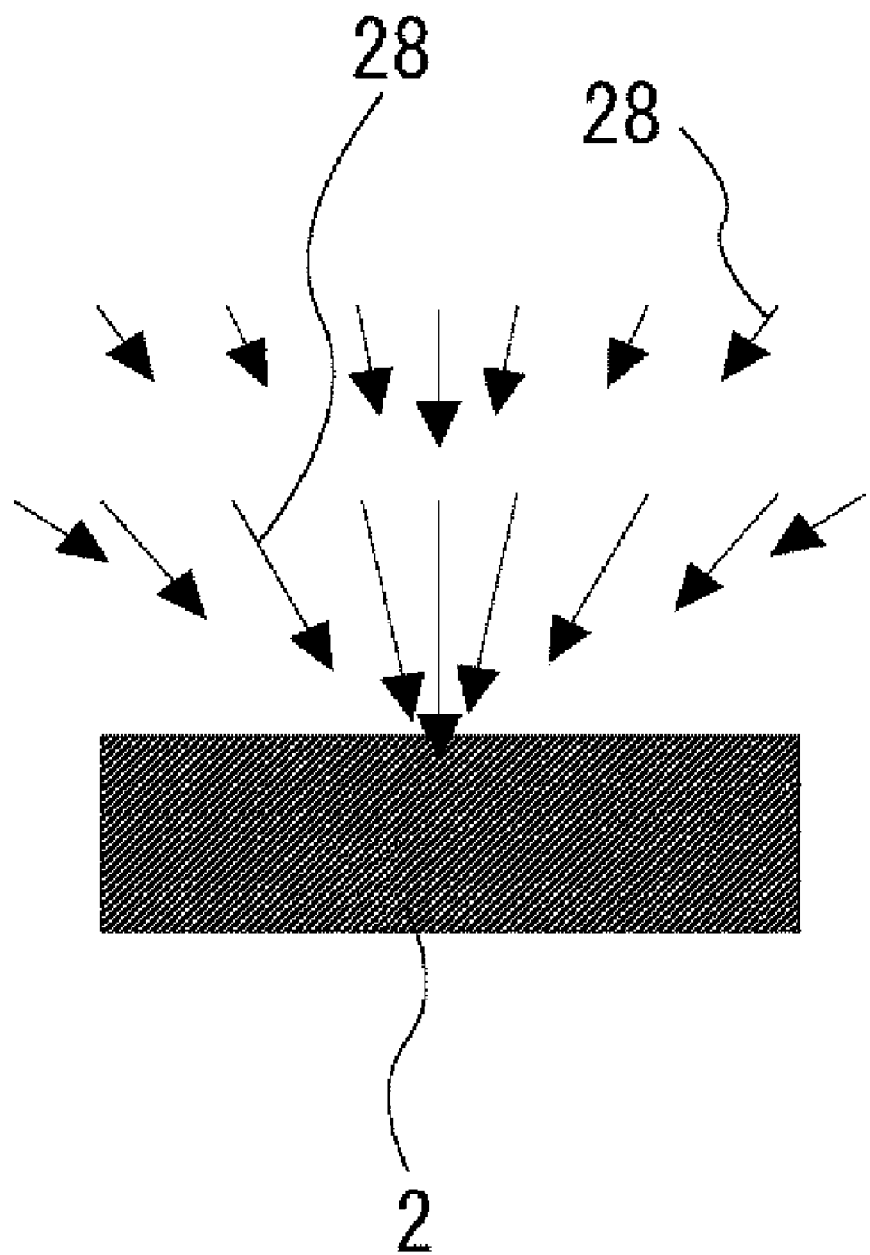
[FIG. 3] This is a view of magnetic force vector distribution in the upper space on the superconductive bulk magnet surface in one example of the invention.

Concrete examples of the invention are described below with reference to the drawings. FIG. 1 to FIG. 3 each show the magnetic induction system of the first embodiment of the invention.

EXAMPLES

The superconductive bulk magnet 2 included in the magnetic field generation means 1 as shown in FIG. 1 comprises the following constituent elements. As the magnetic field generation means 1, for example, shown is a configuration where a YBCO-base superconductive bulk body is used, and the superconductive bulk body is directly cooled with the compressor (now shown)-integrated starling type small-size refrigerator 3 using an operating gas of helium or any other than helium gas such as nitrogen or the like. The outer periphery of the superconductive bulk body is integrated with a stainless or aluminium-made ring 4 with an adhesive or the like so that the superconductive bulk body is prevented from being cracked owing to the magnetic force thereof in magnetizing the bulk body. The superconductive bulk body and the ring 4 are thermally integrated with the heat-transfer flange 5 of copper or aluminium, with an adhesive or the like, and the heat-transfer flange 5 and the heat-transfer flange 6 are thermally integrated via an indium sheet or grease (not shown) with a bolt (not shown) or the like.

The heat-transfer flange 6 is fixed and supported by the cylinder 7 formed with, for example, glass fibers (not shown)—incorporated epoxy resin steel having a small thermal conductivity, and a bolt (not shown) or the like; and the other end of the cylinder 7 is integrated with, for example, the stainless-made flange 8 formed with an adhesive, and the flange 8 is airtightly fixed with the room-temperature flange 9 and an O-ring and a bolt (not shown). The fixation flange 10 of the small-size refrigerator 3 is metallurgically and airtightly integrated with the room-temperature flange 9, and is airtightly fixed with the fixation flange 12 of the small-size refrigerator 3 by an O ring and a bolt (not shown) via the bellow 11 having vacuum airtightness. Around the superconductive bulk body, a vacuum chamber 13 is arranged for vacuum heat insulation, and the flange 14 at the end of the vacuum chamber is airtightly fixed to the flanges 8 and 9 with an O-ring and a bolt (not shown). The cylinder 7 is provided with an inner and outer vacuum discharge hole 15.

Around the superconductive bulk body, the cylinder part 16 of the refrigerator 3 and the cold stage 7 that are to be at an ultra-low temperature of about −230° C. owing to the driving of the small-size refrigerator 3, the radiation insulating materials 17, 17' and 17" are wound for preventing the penetration thereinto of the radiation heat from the constituent members at room temperature. The space 18 is degassed in vacuum via the vacuum duct 20 and the valve 21 by the vacuum pump 19, thereby forming a vacuum adiabatic space. After cooled to ultra-low temperature by the refrigerator, the valve 21 is closed and the superconductive bulk magnet 2 and the vacuum pipe 20 can be separated from each other.

A power is supplied to the small-size refrigerator 3 from the power source unit 22 through the power cord 23, and cooled and operated. Regarding the helium gas compression heat of the compressor to be generated in operating the refrigerator, the coolant cooled in the chiller unit 24 is fed via the duct 25, and the coolant thus having absorbed the compression heat is collected in the chiller unit 24 via the duct 26. The helium refrigerator 3 is operated while degassing the space 18 in vacuum, and the superconductive bulk body can be thereby kept at an ultra-low temperature of about −230° C.

For magnetizing the superconductive bulk body, separately prepared is a superconductive magnet for magnetization capable of generating the predetermined magnetic field for the intended magnetization, for example, a magnetic field of 10 Tesla, or a normal conductive magnet of generating a small magnetic field (the two magnets are not shown). Before cooled, the superconductive bulk magnet 2 with the superconductive bulk body incorporated therein is inserted into a magnetic field in the magnet for magnetization that has already generated the magnetic field in which the body is desired to be magnetized, and thereafter, the superconductive bulk body is cooled with the small-size refrigerator 3 to a temperature not higher than the superconductivity temperature. In this, the cylindrical axis direction of the superconductive bulk body is made to correspond to the direction of the main magnetic field to be generated by the magnet for magnetization.

Subsequently, when the magnetic field of the magnet for magnetization is erased, then the magnetic field is trapped in the superconductive bulk body being kept cooled, and so far as the cooling is kept as such, the superconductive bulk magnet 2 of which the magnetic field is on the same level as the magnetic field for magnetization is thereby provided. In that manner, the superconductive bulk body having trapped such a high magnetic filed of, for example, from 5 Tesla to 10 Tesla can be used as the magnetic field generation means 1.

FIG. 2 shows generated magnetic field distribution on the superconductive bulk magnet surface in one example of the invention. In FIG. 2, I indicates the intensity of the magnetic field in the direction perpendicular to the superconductive bulk magnet surface; d indicates the distance in the radial direction from the center of the superconductive bulk magnet end face; and m indicates the center of the superconductive bulk magnet end face. The magnetic field distribution of the superconductive bulk magnet 2 thus magnetized in the manner as above is formed of the aggregation of the microscopic magnetic fluxes distributed almost uniformly and, therefore, for example, in a case where the cross section of the superconductive bulk body is circular, the magnetic field intensity characteristic 27 in the direction perpendicular to the plane of the magnet surface is nearly conical, as shown in the magnetic field distribution map of FIG. 2, and the magnetic filed in the center part is the strongest while that in the outer peripheral part becomes nearly zero. Accordingly, the magnet has an extremely large magnetic field gradation profile in the vertical direction and in the radial direction from the center of the superconductive bulk body. Consequently, as shown in FIG. 3, the magnetic force that is a product of the magnetic field intensity and the magnetic field inclination may be shown by the vector lines 28. Concretely, as in the drawing, the strength of the magnetic force is indicated by the length, and the direction in which the magnetic force acts is indicated by the arrow in the vector lines. As indicated by the vector lines, an extremely large magnetic force is generated in the upper space from the end part of the superconductive bulk body, toward the center part of the end face of the superconductive bulk body from the space in which the magnetic field has passed, in the vertical direction and in the radial direction.

In case where the superconductive bulk magnet 2 is set outside the inner side of the knee of a patient, the magnetic field generated by the superconductive bulk magnet 2 can penetrate into the inside of the body through the skin of the patient, and can therefore penetrate into the damaged recess site of the joint cartilage injured part having neither blood vessel nor nerve tissue and therefore having no self-repairing capability.

On the other hand, for preparing the magnetic complex to be used for medical treatment, the mesenchymal stem cells of a patient that could be changed into the bone, the cartilage, the muscle or the like of the patient are taken out of the body, the surfaces of magnetite fine particles for use as a contrast medium or the like are coated with, for example, a peptide or the like, and the two are mixed in a liquid for a predetermined period of time to thereby prepare a complex of the stem cells bonding to the magnetite fine particles via the peptide.

Figure 4:
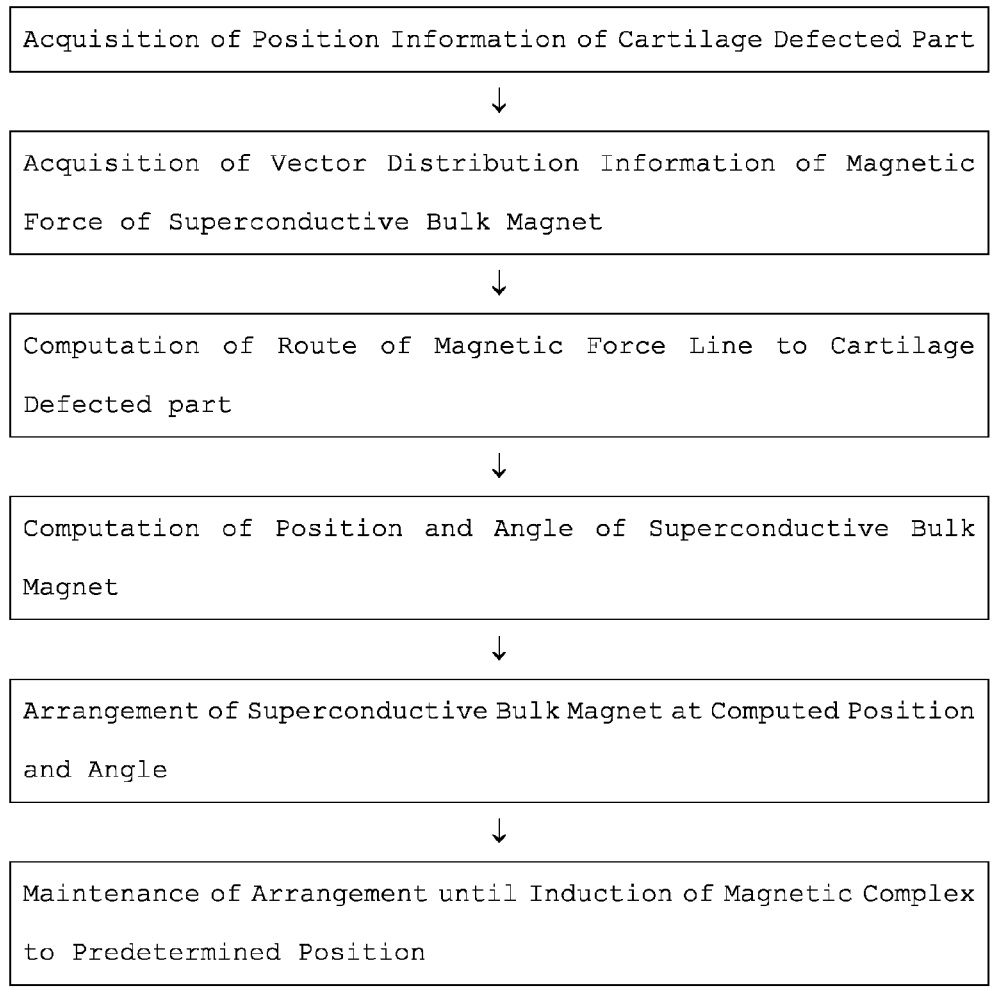
[FIG. 4] This is a view showing the operation flowchart of the magnetic induction system of one example of the invention.
Figure 5:
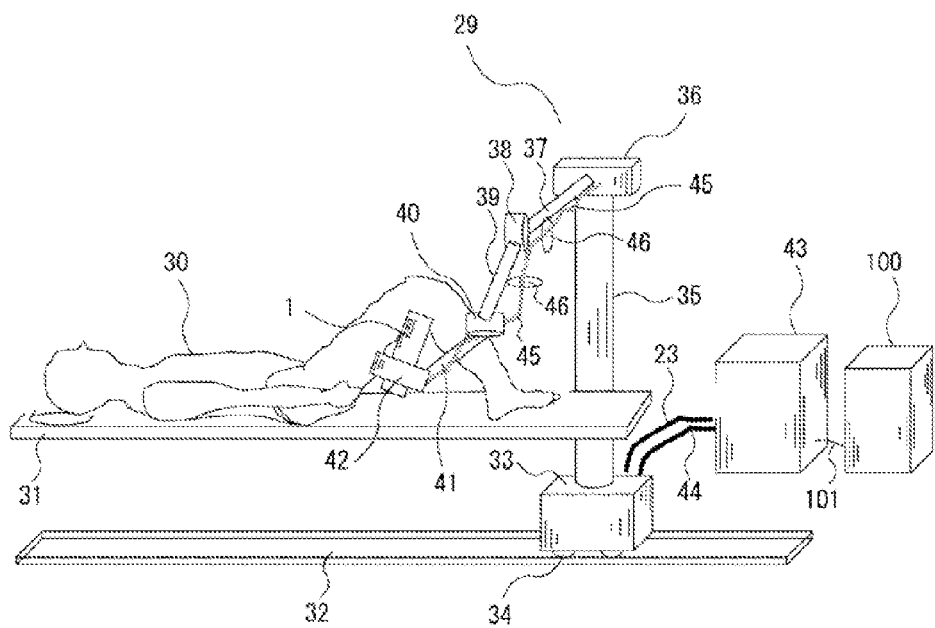
[FIG. 5] This is a view of illustrating the magnetic induction system of one example of the invention.

One example of the magnetic induction system of the invention and the operation flowchart with the system are shown in FIG. 4 and FIG. 5, respectively. In the magnetic induction system of this example, the superconductive bulk magnet 2 is installed in a controlled manner as follows: Using the information of the position of the cartilage defected part of a patient as previously obtained from an X-ray imaging apparatus (not shown) or a nuclear magnetic resonance imaging apparatus (not shown), and the information of magnetic force vector distribution indicating the intensity and the direction of the magnetic force of the superconductive bulk magnet 2 as previously computed or obtained through measurement, the route of the line of the magnetic force from the position in which the magnetic complex has been injected into the body, as previously inputted as the position information, to the cartilage defected part is computed in the computing means 100, and further, the position and the angle of the superconductive bulk magnet necessary for route creation is computed, and while the superconductive bulk magnet 2 is kept at the tip of the superconductive bulk magnet position control unit 29, the magnet part at the tip of the unit is positioned, as controlled at the computed predetermined three-dimensional position and at the computed predetermined angle based on the computed results. Further, the installation is kept as such until the magnetic complex is inducted to the predetermined site in the body.

FIG. 5 is a view showing the magnetic induction system of one example of the invention. The superconductive bulk magnet position control unit 29 is controlled from the computing means 100, for example, by the wireless signal or the wired cable 101. The superconductive bulk magnet position control unit 29 is moved to the predetermined position by the vehicle unit 34 that is rotated and driven by the drive part housing box 33 with a motor (not shown) built therein, on the movable platen 32 near the bed 31 on which the patient 30 is put. Further, the rotary driving part 36 with a rotary motor (not shown) built therein above the support pole 35, the arm 37, the rotary joint part 38, the arm 39, the rotary joint part 40, and the arm 41 are operated to move the superconductive bulk magnet holder 42, whereby the superconductive bulk magnet 2 is again set at the predetermined three-dimensional position as computed by the computing means 100.

In this, the small-size refrigerator power source 22 and the coolant chiller unit 24 shown in FIG. 1 are arranged in the housing box 43, and the feed line 23 and the coolant ducts 25 and 26 are bound up and housed in the protective tube 44, and the two are, after having passed through the inside of the support pole 35 and the upper rotary drive part 36, bundled up and housed in the protective tube 45 formed of a flexible, for example, bellows-like polymer material, and are connected with the superconductive bulk magnet 2. The protective tube 45 is held, as kept passing through the support rings 46 fixed to the arm.

Figure 6:
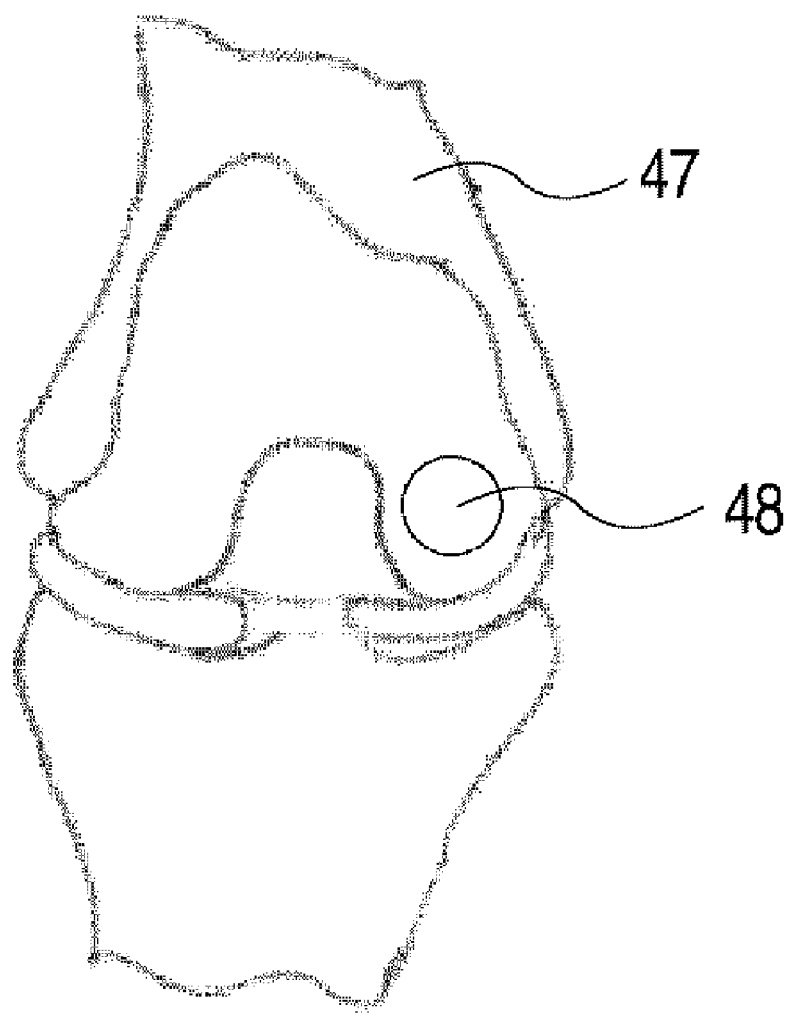
[FIG. 6] This is a view showing the bone and the cartilage defected part of the bone of the thighbone of a knee.
Figure 7:
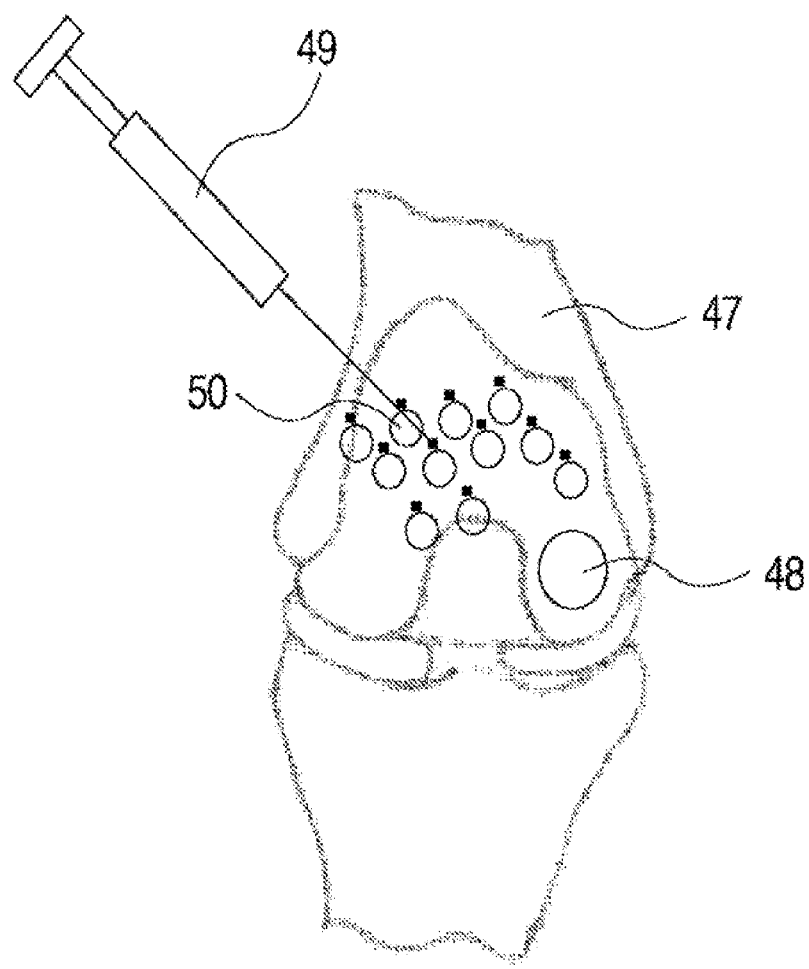
[FIG. 7] This is a view showing the condition of a magnetic complex that has spread and has been distributed in the jelly-like body fluid in a joint.
Figure 8:
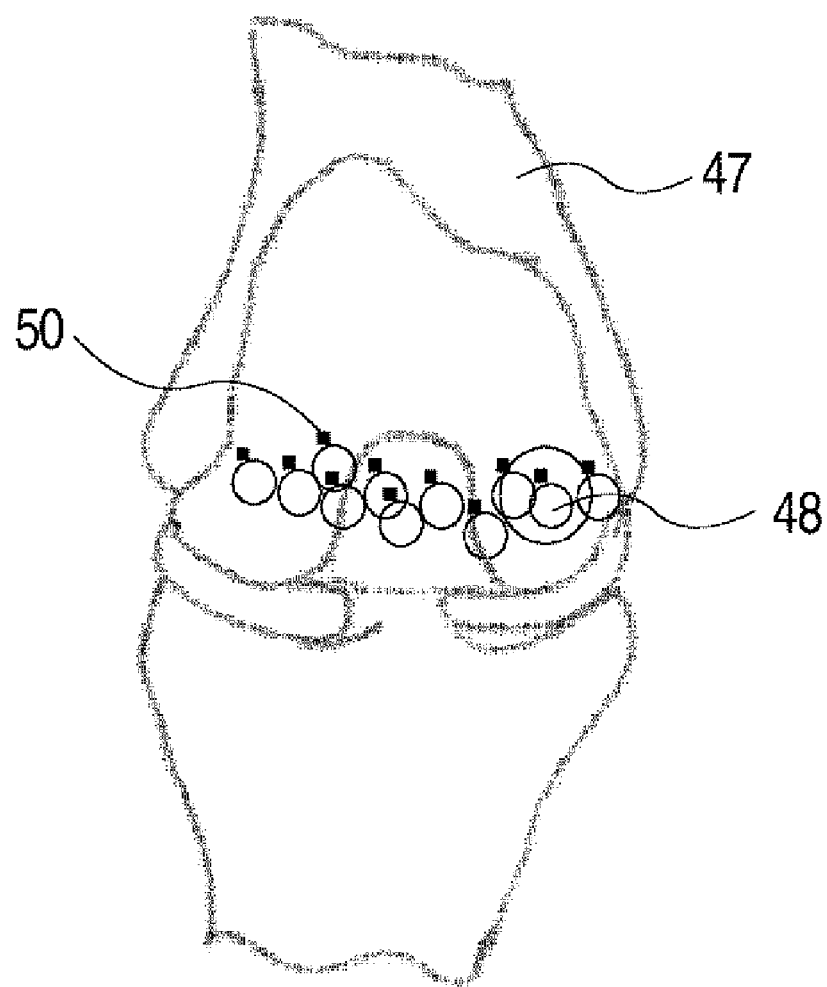
[FIG. 8] This is a view showing the result of in-vivo magnetic induction of a magnetic complex according to a conventional technique.
Figure 9:
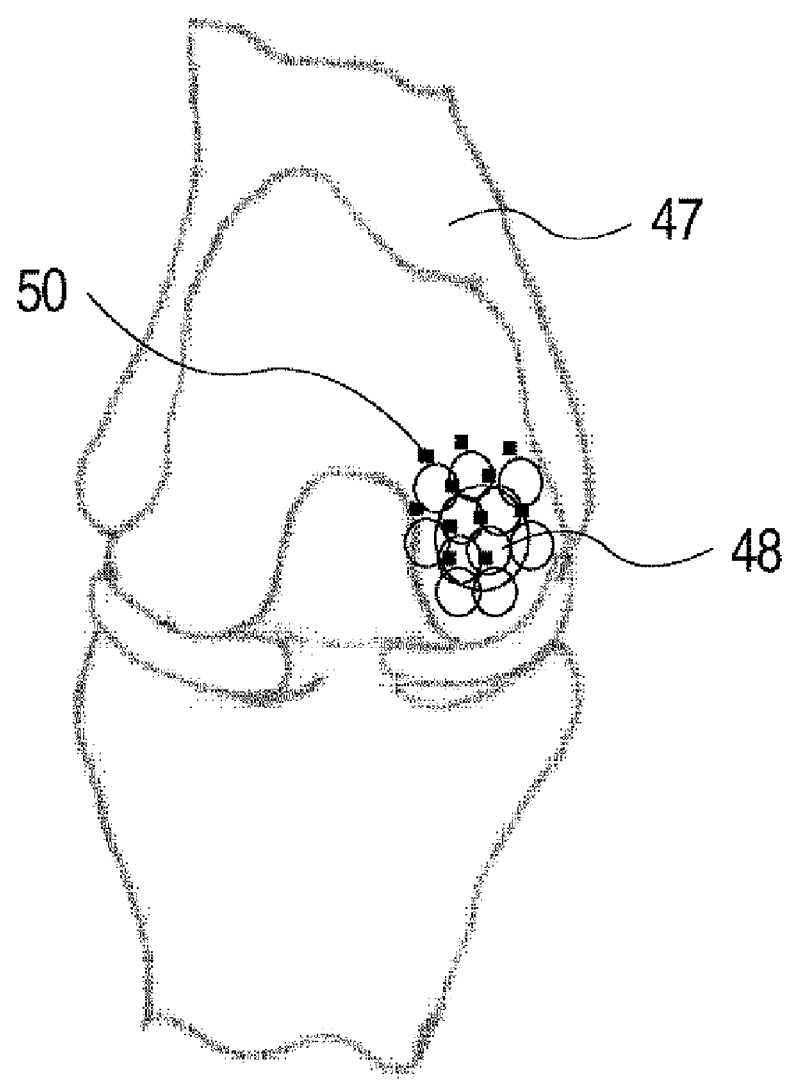
[FIG. 9] This is a view showing the result of in-vivo magnetic induction of a magnetic complex according to the magnetic induction system of one example of the invention.

As in FIG. 5 to FIG. 10 (of which FIG. 8 shows a case of conventional technique), in-vivo magnetic induction of a magnetic complex is attained as follows: With the superconductive bulk magnet position control unit 29, the magnet face of the superconductive bulk magnet 2 is arranged at the predetermined position and angle near the predetermined affected part on the inner side of the knee of the patient 30, and then, as shown in FIG. 6 where the cartilage defected part 48 that has caved in like a circular recess exists on the left side, as seen from the patient 30, above the thigh bone 47 of the knee, the magnetic complex 50 is injected into the predetermined position using the syringe 49 or the like. The injected magnetic complex is, while spreading in the jelly-like body liquid of the joint part, distributed therein, as shown in FIG. 7. In this where a conventional solenoid coil magnet that generates a magnetic field like a ring is arranged on the inner side of the knee, the complex accumulates like a ring in accordance with the magnetic field distribution as shown in FIG. 8, and only a part of the injected magnetic complex 50 could accumulate only in a part of the cartilage defected part 48; however, in this example using multiple magnetic field generation means 1, the magnetic fields can be concentrated in the desired position (FIG. 11), and therefore as shown in FIG. 9, almost all of the injected magnetic complex 50 can be concentrated and accumulated only in the cartilage defected part 48. In that manner, owing to the magnetic force of the superconductive bulk magnet, the magnetic complex 50 that has been widely and statically distributed outside the blood vessel in the body can be magnetically inducted in the cartilage defected part of the affected part, and for example, by keeping the magnetic force for several tens minutes, the complex can be implanted on the bone tissue surface of the surface of the defected part. With that, the magnetic induction operation finishes.

Figure 10:
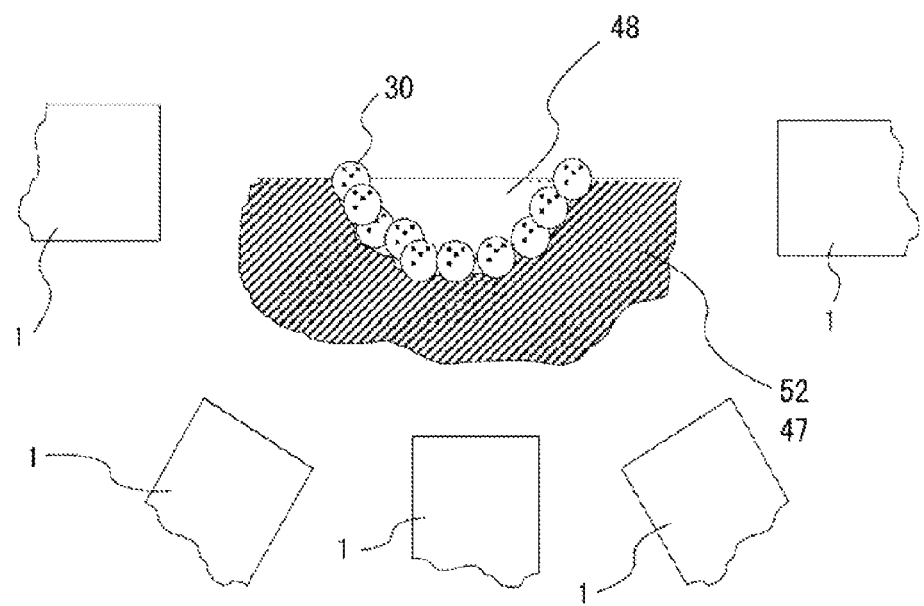
[FIG. 10] This is a view showing the condition of uniformly implanting a magnetic complex on the surface of a cartilage defected part by repeating multiple times the operation of magnetic induction.

The implantation condition of the magnetic complex can be determined by inspecting the implantation density distribution status of the magnetic particles of the magnetic complex in the cartilage defected part 48, using a separate nuclear magnetic resonance imaging apparatus (not shown) or the like, and when an implantation density insufficient part with the magnetic complex is found, then the magnet face of the superconductive bulk magnet 2 is again arranged in the affected part around the inside of the knee of the patient, at the predetermined position and angle thereto as controlled by the superconductive bulk magnet position control unit 29, as shown in FIG. 10, and the magnetic complex is again injected into the reset part using a syringe or the like, and magnetic complex thus re-injected to the implantation insufficient part is magnetically inducted in an adequate manner. This operation is repeated multiple times whereby the magnetic complex can be uniformly implanted on the surface of the cartilage defected part at the predetermined density with reducing the empty space as much as possible.

After the implantation, the patient is kept quiet in bed. With that, the stem cells implanted in the cartilage defected face uniformly at the predetermined density therein then self-propagate to be cartilage cells in about several weeks to fill up the space of the defected part, whereby the cartilage is restored to the original cartilage form in a short period of time and can be cured early.

In this example, as in the above, the superconductive bulk magnet that constitutes the field generation means 1 can magnetically induct the magnetic complex to the predetermined spot position in a three-dimensional space at the predetermined angle thereto, different from a solenoid coil magnet, and therefore, a given amount of the magnetic complex can be uniformly implanted on the surface of the cave of the cartilage defected part at the predetermined density with reducing the empty space as much as possible. To that effect, the invention is effective for restoring the cartilage to the original condition in a short period of time for early curing.

In this example, an electric power or gas power-assisted motor is used for moving the superconductive bulk magnet; however, a weight balancer may be built in the apparatus so that the magnet can be moved by hand, and the case also brings about the same effect. In this case, the position information of the superconductive bulk magnet could be expressed as the information computed by the computing means from the information of the rotary angle of the arm joint part; or a superconductive bulk magnet tip position sensor may be fitted to the apparatus, from which the information is transferred wirelessly, and the information computed by the computing means from the thus-transferred information may be expressed; or the movement operator may control the system through visual check.

In this example, the linear distance between the position of the magnet and the patient is kept constant; however, in case where the magnetic complex 50 is injected in the preset position using the syringe 49 or the like, the injected magnetic complex may be uniformly distributed through self-diffusion by reducing the magnetic force by prolonging the above-mentioned linear distance, in the initial stage for the purpose of uniformly spreading the magnetic complex in the jelly-like body fluid of the joint part, and thereafter the linear distance may be shortened to increase the magnetic force acting on the magnetic complex, whereby the magnetic complex may be uniformly implanted on the broad area of the cartilage defected part 48 that has been recessed like a circular cave.

Figure 11:
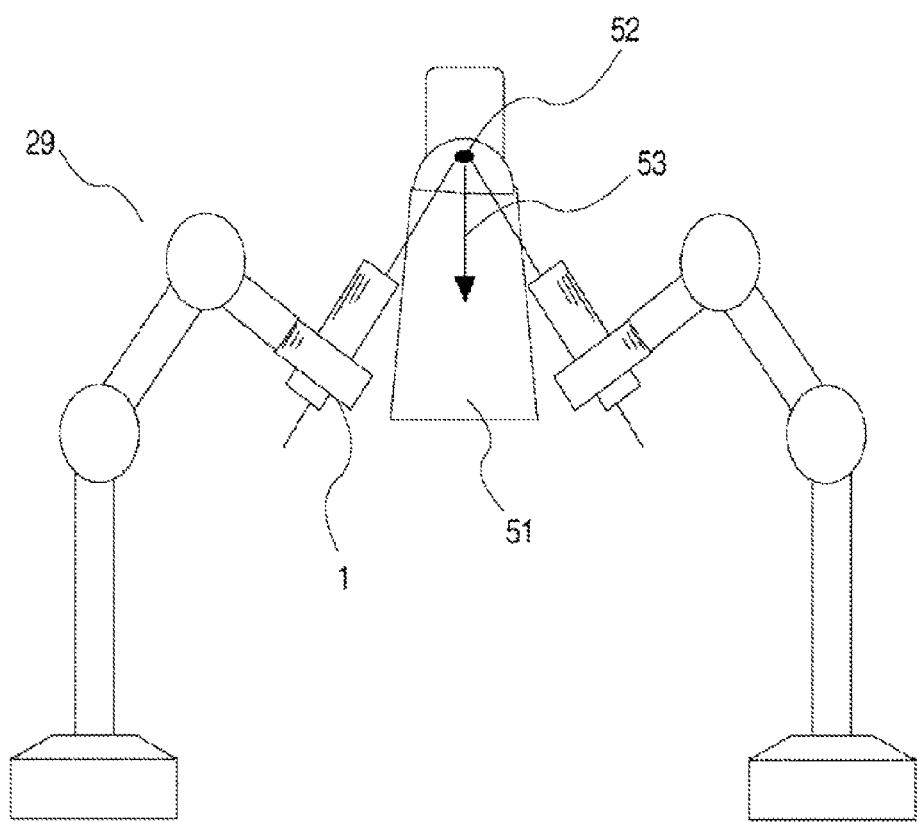
[FIG. 11] This is a view showing one example of the magnet-installed structure in one example of the invention.

FIG. 11 shows one example of the invention. This drawing indicates a magnet installation configuration for the case where the affected part 52 of the knee 51 in the body of the patient has the opening part of the cartilage defected part in the lengthwise direction of the bone and where the superconductive bulk magnet 2 cannot be installed on the back of the bottom of the defected part as the body of the patient interferes with the installation. In this, two superconductive bulk magnet position control units 29 are used, and the superconductive bulk magnet 2 supported by each superconductive bulk magnet position control unit 29 is arranged on both sides of the knee 51, or that is, the two superconductive bulk magnets 2 are so arranged that the resultant force vector 53 of the magnetic force in the magnetic field could act on the opening face of the knee 52. In this example, when the magnetic complex is injected with a syringe or the like in the position upstream the resultant force vector 53 of the magnetic force, then the injected magnetic complex could be accumulated in the affected part 52 along the line of the action of the magnetic force.

Figure 12:
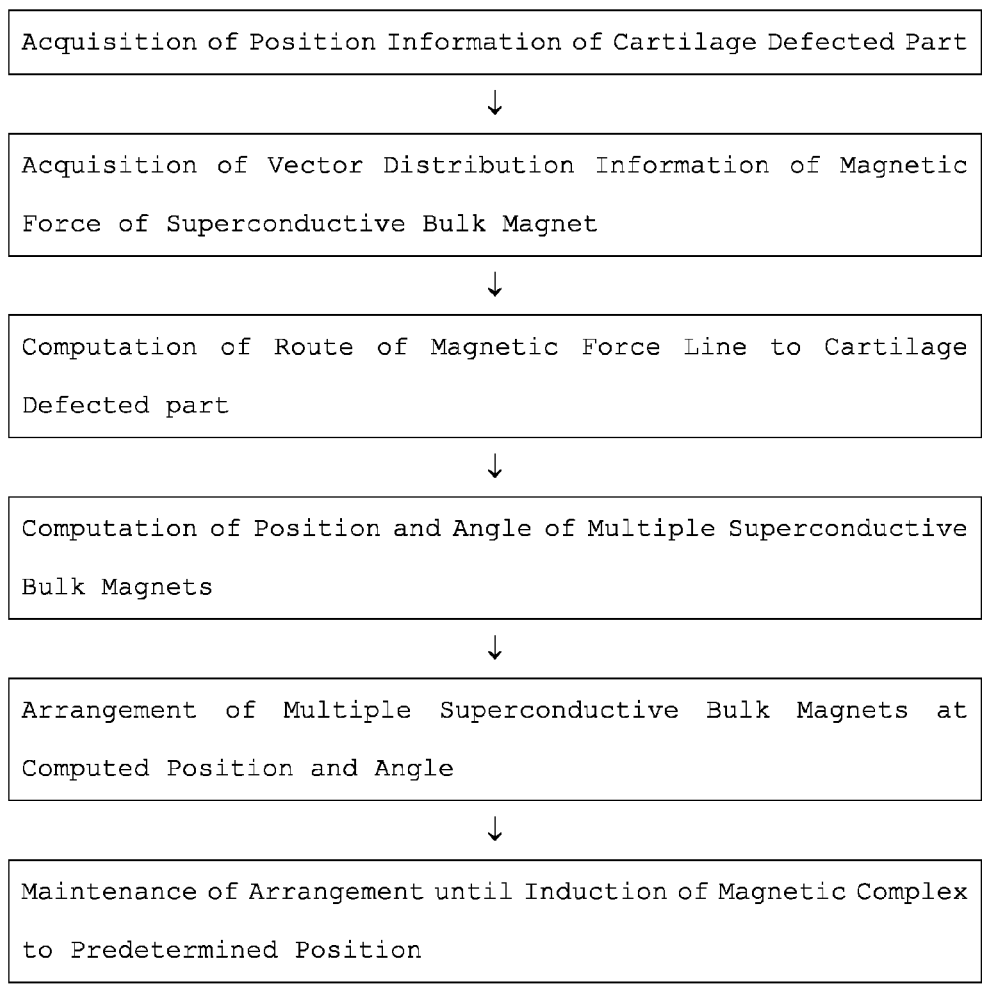
[FIG. 12] This is a view showing the operation flowchart of the magnetic induction system of one example of the invention.

FIG. 12 shows the operation flowchart of the magnetic induction system of another example of the invention. In the multiple magnetic field generation means 1, the superconductive bulk magnet 2 generates a magnetic field. The drive control means has the computing means 100, and, using the information of the position of the cartilage defected part of a patient as previously obtained from an X-ray imaging apparatus (not shown) or a nuclear magnetic resonance imaging apparatus (not shown), and the information of magnetic force vector distribution indicating the intensity and the direction of the magnetic force of the multiple superconductive bulk magnets 2 as previously computed or obtained through measurement, the computing means 100 computes the route of the line of the magnetic force from the position in which the magnetic complex has been injected into the body, as previously inputted as the position information, to the cartilage defected part.

Further, the computing means 100 computes the position and the angle of the multiple superconductive bulk magnets necessary for route creation, and while the superconductive bulk magnet 2 is kept at the tip of the superconductive bulk magnet position control unit 29, the magnet part at the tip of the unit is positioned, as controlled at the computed predetermined three-dimensional position and at the computed predetermined angle based on the computed results.

Figure 13A:
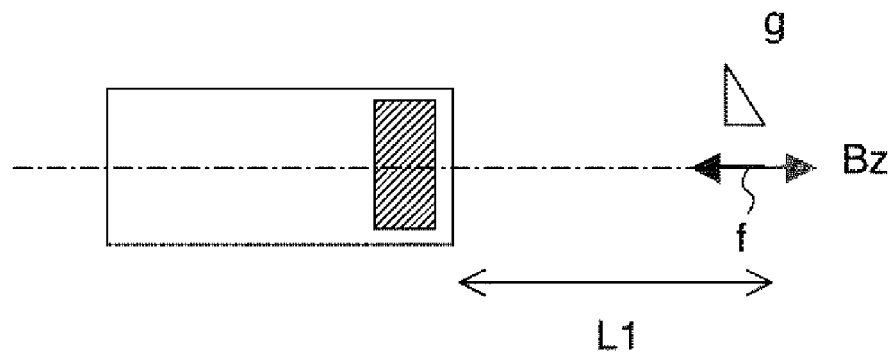
[FIG. 13A] This is a view illustrating an example of using one superconductive bulk magnet in the magnetic induction system of the invention.

FIG. 13A shows an example of using one superconductive bulk magnet in the magnetic induction system of the invention. In FIG. 13A, f indicates the magnetic force vector, Bz indicates the magnetic field intensity, g indicates the magnetic inclination, and L1 indicates the distance from the magnet surface. In case where one superconductive bulk magnet is used in the system with a surface magnetic field of 5 T, the magnetic field intensity Bz at the center position of L1=5 cm from the magnet surface is 0.8 Tesla (T) and the magnetic inclination was recorded as g=dBz/dz=1 (T/cm). In this case, the magnetic force vector f faces in the direction of the superconductive bulk density, and owing to this force, the magnetic bead-inductee complex can be inducted in the bulk magnet direction. The intensity of the magnetic force vector f was recorded as 0.8 ($T^2$/cm).

Figure 13B:
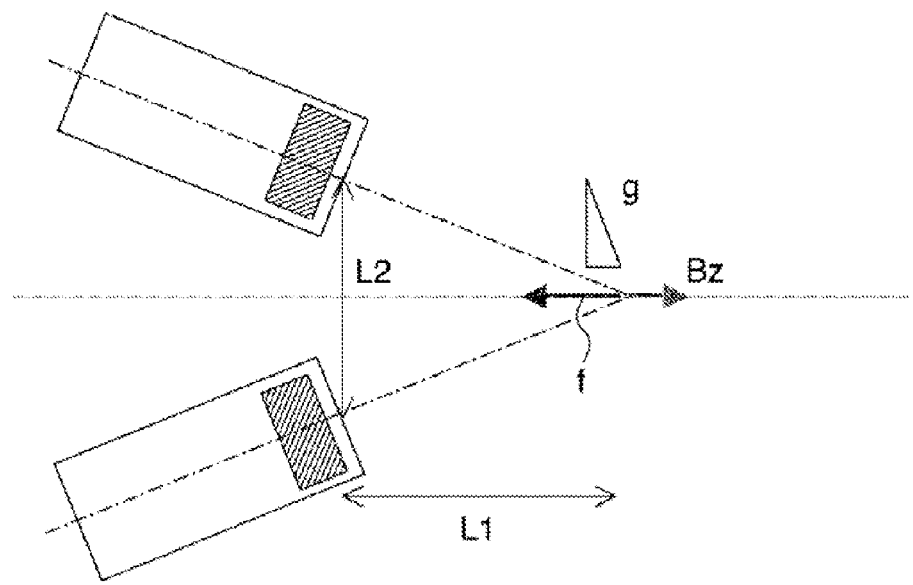
[FIG. 13B] This is a view illustrating an example of using two superconductive bulk magnets in the magnetic induction system of the invention.
Figure 13C:
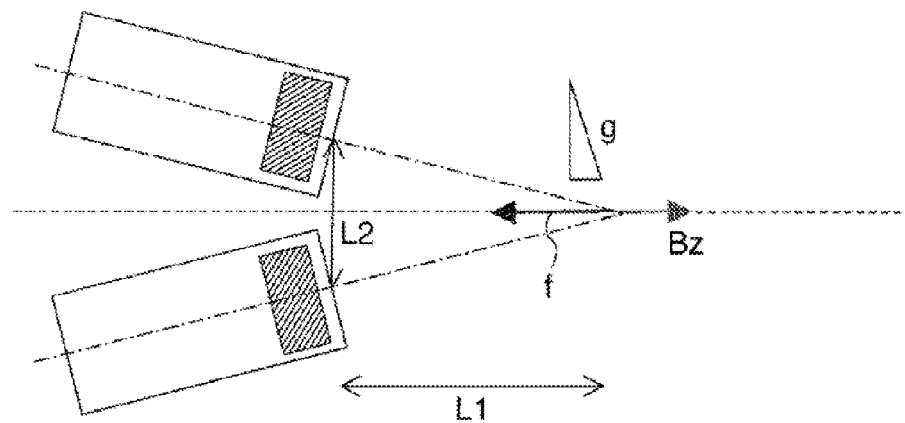
[FIG. 13C] This is a view illustrating an example of controlling the distance between two superconductive bulk magnets to thereby control the vector of the magnetic force, in the magnetic induction system of the invention.

FIG. 13B shows an example of using two superconductive bulk magnets in the magnetic induction system of the invention. In FIG. 13B and FIG. 13C to be mentioned below, f indicates the magnetic force vector, Bz indicates the magnetic field intensity, g indicates the magnetic inclination, L1 indicates the distance from the magnet surface of the first superconductive bulk magnet, and L2 indicates the center-to-center distance between the first superconductive bulk magnet and the second superconductive bulk magnet. Using the system where the two superconductive bulk magnets were processed for excitation in the same manner as in FIG. 13A, in which the center-to-center distance between the two magnets, L2 is 5.8 cm, the axis of the magnet is kept at the position spaced by L1=5 cm from the center of the axis of the magnetic field, and the same pole of the two magnets is kept in the same direction, the magnetic field intensity Bz at that position was measured. The intensity was recorded as 1.4 Tesla (T), and the magnetic inclination g was recorded as g=dBz/dz=1.81 (T/cm). These magnetic field and magnetic inclination have the vector f turning to the center of the two magnets. The intensity of the magnetic force vector f was recorded as 2.5 ($T^2$/cm).

As described above, using two superconductive bulk magnets gives a higher magnetic field intensity and a larger magnetic inclination and therefore gives a larger magnetic force than using one magnet.

FIG. 13C shows an example of controlling the distance between two superconductive bulk magnets to thereby control the vector of the magnetic force, in the magnetic induction system of the invention. Controlling the distance between two superconductive bulk magnets makes it possible to control the magnetic force and the direction in which the magnetic force acts. Using the system with two superconductive bulk magnets both excited in the same manner, in which the center-to-center distance between the two magnets L2 is 4 cm, the axis of the magnet is kept at the position spaced by L1=5 cm from the center of the axis of the magnetic field, and the same pole of the two magnets is kept in the same direction, the magnetic field intensity Bz at that position was measured. The intensity was recorded as 1.8 Tesla (T), and the magnetic inclination g was recorded as g=dBz/dz=2.3 (T/cm). These magnetic field and magnetic inclination have the vector f turning to the center of the two magnets. The intensity of the magnetic force vector f was recorded as 4.1 ($T^2$/cm).

As described above, controlling the distance between superconductive magnets makes it possible to control the magnetic force at the position at which the cartilage regeneration is intended. Further, depending on controlling the magnet arrangement, controlling the direction vector of the magnetic force is needed.

Figure 13D:
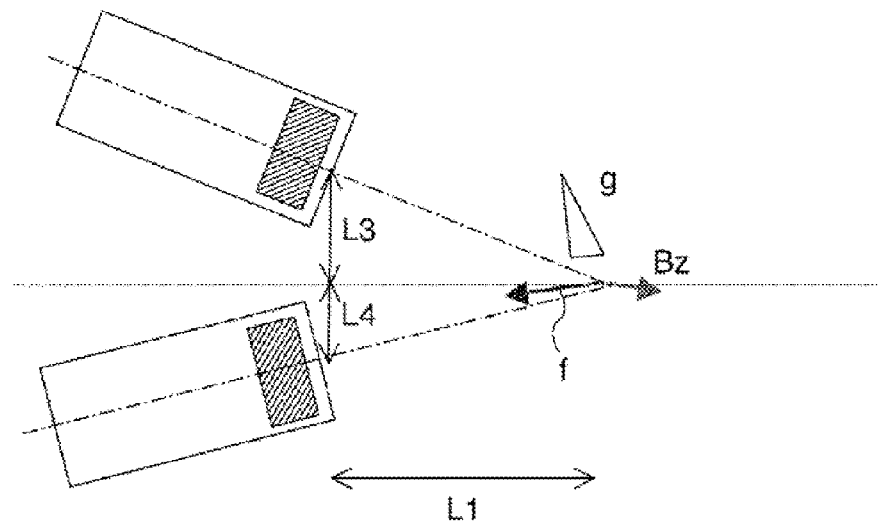
[FIG. 13D] This is a view illustrating another example of controlling the distance between two superconductive bulk magnets to thereby control the vector of the magnetic force, in the magnetic induction system of the invention.

FIG. 13D shows another example of controlling the distance between two superconductive bulk magnets to thereby control the vector of the magnetic force, in the magnetic induction system of the invention. In FIG. 13D, L3 indicates the distance from the first superconductive bulk magnet 2 to the center axis, and L4 indicates the distance from the second superconductive bulk magnet 2 to the center axis. f indicates a magnetic force vector, Bz indicates the magnetic field intensity, g indicates the magnetic inclination, L1 indicates the distance from the magnet surface of the first superconductive bulk magnet, and L2 indicates the center-to-center distance between the first superconductive bulk magnet and the second superconductive bulk magnet. Using the system where the two superconductive bulk magnets were processed for excitation in the same manner as in FIG. 13C, in which the magnet 2 is arranged at the position spaced by L3=2.9 cm from the center, the magnet 2 is arranged at the position spaced by L4=2 cm from the center, the axis of each magnet is kept at the position spaced by L1=5 cm from the center of the axis of the magnetic field, and the same pole of the two magnets is kept in the same direction, the magnetic field intensity Bz at that position was measured. In that case, the highest magnetic field intensity Bz was 1.6 Tesla (T), and its vector shifted from the position toward the direction of the nearer magnet, as illustrated. The highest magnetic inclination g was recorded as g=dBz/dz=2.04 (T/m), and its vector f also shifted in the same direction as illustrated. The intensity of the magnetic force f was recorded as 3.3 ($T^2$/cm). In that manner, changing the relative position of the magnets makes it possible to control the magnetic force intensity and also the vector in which the force acts.

Changing the two magnets makes it possible to change the direction and the intensity of the resultant magnetic force vector, therefore enabling magnetic induction of magnetic complex in any desired direction. Accordingly, in this example, the magnetic complex can be adequately accumulated in the affected part 52 even in a case where one superconductive bulk magnet could not attain adequate magnetic induction as impeded by the patient's body.

In this example, the two superconductive magnets have the same polarity so that the two magnets could repel each other depending on the arrangement of the two magnets. Accordingly, the two magnets are prevented from acting on the knee of the patient to catch and injure it between them. Specifically, in an embodiment, the magnetic pole at each magnetic field generation end of the multiple magnetic field generation means 1 may have the same polarity, and the drive control means may be so designed as to be able to control the position and the angle of the multiple magnetic field generation means 1 so that the magnetic fields to be generated by those multiple magnetic field generation means 1 mutually repel each other at the desired position of a living body.

In another embodiment, the drive control means may be so designed as to be able to control the intensity of the magnetic field in the desired position of a living body in accordance with the lapse time after introduction of magnetic complex into the body. In particular, just after introduction of magnetic complex, the magnetic field generation means 1 may be installed at the position somewhat separated from the affected part of the living body in order that the magnetic complex could diffuse in a broad range, by which a relative weak magnetic field is made to act on the affected part, and thereafter in accordance with the lapse time after the introduction, the magnetic field generation means 1 may be moved nearer to the affected part of the living body so that a relatively strong magnetic field could be applied thereto. Accordingly, the magnetic complex can be accumulated in the affected part having a three-dimensional form.

(Example of Production of Superconductive Bulk Magnet)

For realizing the apparatus of the invention, a superconductive bulk magnet excellent in directionality and capable of generating a strong magnetic field at high temperature is needed. For realizing the system, a bulk superconductor having a high critical temperature, excellent in critical current in a high-temperature high-intensity magnetic field and excellent in mechanical characteristics and thermal stability is needed. Examples of producing superconductive bulk bodies suitable to the system are shown below. Table 1 shows a summary of production examples for superconductive bulk bodies.

TABLE 1

(Magnet Production Examples)

| | Magnet Composition | Number of Al Rods | Shape-Memory Alloy-Made Ring | Wood Metal Infiltration | Trapped Magnetic Field |
|---|---|---|---|---|---|
| Production Example 1 | (Nd,Eu,Gd)—Ba—Cu—O | 6 | Fe—Mn—Si | Pb—Bi—Sn | 4 T (surface) |
| Production Example 2 | (Nd,Eu,Gd)—Ba—Cu—O | 6 | — | — | 3.5 T (surface) |
| Production Example 3 | (Nd,Eu,Gd)—Ba—Cu—O | — | — | — | 2 T (surface) |
| Production Example 4 | Gd—Ba—Cu—O | 6 | Fe—Mn—Si | Pb—Bi—Sn | 3 T (surface) |
| Production Example 5 | Gd—Ba—Cu—O | 6 | — | — | 2.5 T (surface) |
| Production Example 6 | Gd—Ba—Cu—O | none | | | 1.2 T (surface) |
| Production Example 7 | Y—Ba—Cu—O | 6 | Fe—Mn—Si | Pb—Bi—Sn—Cd | 1.1 T (surface) |
| Production Example 8 | Y—Ba—Cu—O | 6 | — | — | 1.0 T (surface) |
| Production Example 9 | Y—Ba—Cu—O | — | — | — | 0.5 T (surface) |

Production Example 1

A powder of (Nd, Eu, Gd) $Ba_2Cu_3O_y$ (where $6.8 \leq y \leq 7.0$) and a powder of $(Nd, Eu, Gd)_2BaCuO_5$, in which the mixing ratio of Nd, Eu and Gd was 1/1/1, were prepared, and these compounds were weighed at a ratio of 4/1, and after 0.5% by weight of Pt was added thereto, these were well mixed (step 1001). Subsequently, this was shaped into a pellet having a diameter of 42 mm and a thickness of 15 mm under a hydrostatic pressure of 2000 MPa (step 1002). The pellet was partially sintered by heating in air at 900° C. for 1 hour (step 1003). Next, 6 artificial holes each having a diameter of 2 mm were formed at regular intervals along the circumference spaced by 20 mm from the center of the sintered body, using a carbide drill (step 1004). Next, at the bottom of an $Al_2O_3$-made crucible having a diameter of 50 mm, a pellet formed of an $Nd_2O_3$ powder and having a diameter of 45 mm and a thickness of 2 mm was put, and a pellet formed of a $BaCuO_2$ powder and having a diameter of 45 mm and a thickness of 10 mm was further put thereon (step 1005). On this, the sintered body (Nd, Eu, Gd)—Ba—Cu—O having 6 artificial holes formed therethrough was put (step 1006).

Subsequently, the $Al_2O_3$-made crucible with the sintered body therein was set in an electric furnace having a controlled atmosphere of 1% $O_2$+99% Ar, and a single crystal of $NdBa_2Cu_3O_y$ having a size of 2 mm square and a thickness of 1 mm was set as a seed at the center of the sintered body (Nd, Eu, Gd)—Ba—Cu—O (step 1007). Subsequently, this was heated up to 1100° C. in an electric furnace at a speed of 50° C./hr, then soaked as such for 1 hour, and cooled to 1050° C. taking 1 hour, and afterwards, this was gradually cooled to 950° C. at a speed of 0.2° C./hr, and then kept cooled as such in the furnace (step 1008). The sample taken out of the furnace was finally annealed with oxygen in a 100% oxygen current atmosphere at 300° C. for 100 hours (step 1009). In this state, the superconductive critical temperature of the sample was measured and was 95 K.

Next, 6 aluminium rods each having a diameter of 1.8 mm and a length of 20 mm were inserted into the artificial holes (step 1010). Subsequently, a Pb—Bi—Sn alloy was heated at 200° C. and infiltrated into the sample by degassing with a vacuum pump (step 1011). An Fe—Mn—Si shape-memory alloy-made ring having an inner diameter of 19 mm, a thickness of 3 mm and a height of 20 mm was arranged around the bulk body and the Pb—Bi—Sn alloy was heated at 300° C., and then by degassing with a vacuum pump, pre-compression with the shape-memory alloy and vacuum infiltration were attained at the same time (step 1012).

As a result, the (Nd, Eu, Gd)—Ba—Cu—O superconductive bulk magnet that had been complexed with the aluminium rods and given a pre-compression load with the Fe—Mn—Si shape-memory alloy-made ring provided a trapped magnetic field of 4 T on the surface thereof.

Production Example 2

According to the same process of from (step 1001) to (step 1010) as in the above-mentioned Production Example 1, a superconductive bulk body of (Nd, Eu, Gd)—Ba—Cu—O was formed. Also in Production Example 2, 6 aluminium rods each having a diameter of 1.8 mm and a length of 20 mm were inserted into the artificial holes. The difference from Production Example 1 is that the process herein was not followed by the step of heating the Pb—Bi—Sn alloy at 200° C. and infiltrating it by degassing with a vacuum pump (step 1011) and by the step of arranging the Fe—Mn—Si shape-memory alloy-made ring around the bulk body, heating the Pb—Bi—

Sn alloy at 300° C. and thereafter degassing the system with a vacuum pump for simultaneously attaining the pre-compression with the shape-memory alloy and vacuum infiltration (step 1012).

The (Nd, Eu, Gd)—Ba—Cu—O superconductive bulk magnet that had been complexed with the aluminium rods, as produced in Production Example 2, provided a trapped magnetic field of 3.5 T on the surface thereof.

Production Example 3

According to the same process of from (step 1001) to (step 1009) as in the above-mentioned Production Example 1, a superconductive bulk body of (Nd, Eu, Gd)—Ba—Cu—O was formed. The difference from Production Example 1 is that the process herein was not followed by the step of inserting the 6 aluminium rods each having a diameter of 1.8 mm and a length of 20 mm into the artificial holes (step 1010), by the step of heating the Pb—Bi—Sn alloy at 200° C. and infiltrating it by degassing with a vacuum pump (step 1011) and by the step of arranging the Fe—Mn—Si shape-memory alloy-made ring around the bulk body, heating the Pb—Bi—Sn alloy at 300° C. and thereafter degassing the system with a vacuum pump for simultaneously attaining the pre-compression with the shape-memory alloy and vacuum infiltration (step 1012). Accordingly, in Production Example 3, aluminium rods were not inserted in the artificial rods.

In Production Example 3, in addition, a superconductive bulk body of (Nd, Eu, Gd)—Ba—Cu—O with no artificial hole was formed. These samples were, while kept given a magnetic field of 5 T with a superconductive magnet, cooled with liquid nitrogen (77 K) for 20 minutes, and then the external magnetic field was lowered at a speed of 0.1 T/min, kept zero for 5 minutes, and thereafter the trapped magnetic field was measured using a two-dimensional scanning magnetic field distribution analyzer.

The (Nd, Eu, Gd)—Ba—Cu—O superconductive bulk magnet not complexed with metal, as produced in Production Example 3, provided a trapped magnetic field of 2 T on the surface thereof.

In Production Examples 1 to 3, the same measurement was repeated. As a result, the (Nd, Eu, Gd)—Ba—Cu—o superconductive bulk magnet that had been complexed with the aluminium rods recorded the same trapped magnetic field irrespective of the presence or absence of the Fe—Mn—Si shape-memory alloy-made ring therein. The (Nd, Eu, Gd)—Ba—Cu—O superconductive bulk magnet not complexed with metal provided a trapped magnetic field of 1.7 T on the surface thereof.

Production Example 4

A powder of $GdBa_2Cu_3O_y$ and a powder of $Gd_2BaCuO_5$ were prepared, and these compounds were weighed at a ratio of 10/3, and after 0.5% by weight of Pt was added thereto, these were well mixed (step 4001). Subsequently, this was shaped into a pellet having a diameter of 42 mm and a thickness of 15 mm under a hydrostatic pressure of 2000 MPa (step 4002). The pellet was partially sintered by heating in air at 900° C. for 1 hour (step 4003). Next, 6 artificial holes each having a diameter of 2 mm were formed at regular intervals along the circumference spaced by 20 mm from the center of the sintered body, using a carbide drill (step 4004). Next, at the bottom of an $Al_2O_3$-made crucible having a diameter of 50 mm, a pellet formed of a $Gd_2O_3$ powder and having a diameter of 45 mm and a thickness of 2 mm was put, and a pellet formed of a $BaCuO_2$ powder and having a diameter of 45 mm and a thickness of 10 mm was further put thereon (step 4005). On this, the sintered body Gd—Ba—Cu—O having 6 artificial holes formed therethrough was put (step 4006).

Subsequently, the $Al_2O_3$-made crucible with the sintered body therein was set in an electric furnace having a controlled atmosphere of 1% $O_2$+99% Ar, and a single crystal of $NdBa_2Cu_3O_y$ having a size of 2 mm square and a thickness of 1 mm was set as a seed at the center of the sintered body Gd—Ba—Cu—O (step 4007). Subsequently, this was heated up to 1100° C. in an electric furnace at a speed of 50° C./hr, then soaked as such for 1 hour, and cooled to 1055° C. taking 1 hour, and afterwards, this was gradually cooled to 950° C. at a speed of 0.2° C./hr, and then kept cooled as such in the furnace (step 4008). The sample taken out of the furnace was finally annealed with oxygen in a 100% oxygen current atmosphere at 300° C. for 100 hours (step 4009). In this state, the superconductive critical temperature of the sample was measured and was 94 K.

Next, 6 aluminium rods each having a diameter of 1.8 mm and a length of 20 mm were inserted into the artificial holes (step 4010). Subsequently, a Pb—Bi—Sn alloy was heated at 200° C. and infiltrated into the sample by degassing with a vacuum pump (step 4011). An Fe—Mn—Si shape-memory alloy-made ring having an inner diameter of 19 mm, a thickness of 3 mm and a height of 20 mm was arranged around the bulk body and the Pb—Bi—Sn alloy was heated at 300° C., and then by degassing with a vacuum pump, pre-compression with the shape-memory alloy and vacuum infiltration were attained at the same time (step 4012).

As a result, the Gd—Ba—Cu—O superconductive bulk magnet that had been complexed with the aluminium rods and given a pre-compression load with the Fe—Mn—Si shape-memory alloy-made ring provided a trapped magnetic field of 3 T on the surface thereof.

Production Example 5

According to the same process of from (step 4001) to (step 4010) as in the above-mentioned Production Example 4, a superconductive bulk body of Gd—Ba—Cu—O was formed. Also in Production Example 4, 6 aluminium rods each having a diameter of 1.8 mm and a length of 20 mm were inserted into the artificial holes. The difference from Production Example 4 is that the process herein was not followed by the step of heating the Pb—Bi—Sn alloy at 200° C. and infiltrating it by degassing with a vacuum pump (step 4011) and by the step of arranging the Fe—Mn—Si shape-memory alloy-made ring around the bulk body, heating the Pb—Bi—Sn alloy at 300° C. and thereafter degassing the system with a vacuum pump for simultaneously attaining the pre-compression with the shape-memory alloy and vacuum infiltration (step 4012).

The Gd—Ba—Cu—O superconductive bulk magnet that had been complexed with the aluminium rods, as produced in Production Example 5, provided a trapped magnetic field of 2.5 T on the surface thereof.

Production Example 6

According to the same process of from (step 4001) to (step 4009) as in the above-mentioned Production Example 4, a superconductive bulk body of Gd—Ba—Cu—O was formed. The difference from Production Example 4 is that the process herein was not followed by the step of inserting the 6 aluminium rods each having a diameter of 1.8 mm and a length of 20 mm into the artificial holes (step 4010), by the step of heating the Pb—Bi—Sn alloy at 200° C. and infiltrating it by degassing with a vacuum pump (step 4011) and by the step of arranging the Fe—Mn—Si shape-memory alloy-made ring around the bulk body, heating the Pb—Bi—Sn alloy at 300° C. and thereafter degassing the system with a vacuum pump for simultaneously attaining the pre-compression with the shape-memory alloy and vacuum infiltration (step 4012). Accordingly, in Production Example 6, aluminium rods were not inserted in the artificial rods.

In Production Example 6, in addition, a superconductive bulk body of Gd—Ba—Cu—O with no artificial hole was formed. These samples were, while kept given a magnetic field of 5 T with a superconductive magnet, cooled with liquid nitrogen (77 K) for 20 minutes, and then the external magnetic field was lowered at a speed of 0.1 T/min, kept zero for 5 minutes, and thereafter the trapped magnetic field was measured using a two-dimensional scanning magnetic field distribution analyzer.

The Gd—Ba—Cu—O superconductive bulk magnet not complexed with metal, as produced in Production Example 6, provided a trapped magnetic field of 1.2 T on the surface thereof.

In Production Examples 4 to 6, the same measurement was repeated. As a result, the Gd—Ba—Cu—O superconductive bulk magnet that had been complexed with the aluminium rods recorded the same trapped magnetic field irrespective of the presence or absence of the Fe—Mn—Si shape-memory alloy-made ring therein. The Gd—Ba—Cu—O superconductive bulk magnet not complexed with metal provided a trapped magnetic field of 1.2 T on the surface thereof.

Production Example 7

A powder of $YBa_2Cu_3O_y$ (where $6.8 \leq y \leq 7.0$) and a powder of $Y_2BaCuO_5$ were prepared, and these compounds were weighed at a ratio of 10/3, and after 0.5% by weight of Pt was added thereto, these were well mixed (step 7001). Subsequently, this was shaped into a pellet having a diameter of 42 mm and a thickness of 15 mm under a hydrostatic pressure of 2000 MPa (step 7002). The pellet was partially sintered by heating in air at 900° C. for 1 hour (step 7003). Next, 6 artificial holes each having a diameter of 2 mm were formed at regular intervals along the circumference spaced by 20 mm from the center of the sintered body, using a carbide drill (step 7004). Next, at the bottom of an $Al_2O_3$-made crucible having a diameter of 50 mm, a pellet formed of a $Y_2O_3$ powder and having a diameter of 45 mm and a thickness of 2 mm was put, and a pellet formed of a $BaCuO_2$ powder and having a diameter of 45 mm and a thickness of 10 mm was further put thereon (step 7005). On this, the sintered body Y—Ba—Cu—O having 6 artificial holes formed therethrough was put (step 7006).

Subsequently, the $Al_2O_3$-made crucible with the sintered body therein was set in an electric furnace in air, and a single crystal of $NdBa_2Cu_3O_y$ having a size of 2 mm square and a thickness of 1 mm was set as a seed at the center of the sintered body Y—Ba—Cu—O (step 7007). Subsequently, this was heated up to 1100° C. in an electric furnace at a speed of 50° C./hr, then soaked as such for 1 hour, and cooled to 1050° C. taking 1 hour, and afterwards, this was gradually cooled to 950° C. at a speed of 0.2° C./hr, and then kept cooled as such in the furnace (step 7008). The sample taken out of the furnace was finally annealed with oxygen in a 100% oxygen current atmosphere at 300° C. for 100 hours (step 7009). In this state, the superconductive critical temperature of the sample was measured and was 90 K.

Next, 6 aluminium rods each having a diameter of 1.8 mm and a length of 20 mm were inserted into the artificial holes (step 7010). Subsequently, a Pb—Bi—Sn—Cd alloy was heated at 300° C. and infiltrated into the sample by degassing with a vacuum pump (step 7011). An Fe—Mn—Si shape-memory alloy-made ring having an inner diameter of 19 mm, a thickness of 3 mm and a height of 20 mm was arranged around the bulk body and the Pb—Bi—Sn—Cd alloy was heated at 300° C., and then by degassing with a vacuum pump, pre-compression with the shape-memory alloy and vacuum infiltration were attained at the same time (step 7012).

As a result, the Y—Ba—Cu—O superconductive bulk magnet that had been complexed with the aluminium rods and given a pre-compression load with the Fe—Mn—Si shape-memory alloy-made ring provided a trapped magnetic field of 1.1 T on the surface thereof.

Production Example 8

According to the same process of from (step 7001) to (step 7010) as in the above-mentioned Production Example 7, a superconductive bulk body of Y—Ba—Cu—O was formed. Also in Production Example 8, 6 aluminium rods each having a diameter of 1.8 mm and a length of 20 mm were inserted into the artificial holes. The difference from Production Example 7 is that the process herein was not followed by the step of heating the Pb—Bi—Sn alloy at 200° C. and infiltrating it by degassing with a vacuum pump (step 7011) and by the step of arranging the Fe—Mn—Si shape-memory alloy-made ring around the bulk body, heating the Pb—Bi—Sn alloy at 300° C. and thereafter degassing the system with a vacuum pump for simultaneously attaining the pre-compression with the shape-memory alloy and vacuum infiltration (step 7012).

Precisely, the superconductive bulk body in Production Example 8 was formed as follows: A powder of $YBa_2Cu_3O_y$ (where $6.8 \leq y \leq 7.0$) and a powder of $Y_2BaCuO_5$ were prepared, and these compounds were weighed at a ratio of 10/3, and after 0.5% by weight of Pt was added thereto, these were well mixed. Subsequently, this was shaped into a pellet having a diameter of 42 mm and a thickness of 15 mm under a hydrostatic pressure of 2000 MPa. The pellet was partially sintered by heating in air at 900° C. for 1 hour. Next, 6 artificial holes each having a diameter of 2 mm were formed at regular intervals along the circumference spaced by 20 mm from the center of the sintered body, using a carbide drill. Next, at the bottom of an $Al_2O_3$-made crucible having a diameter of 50 mm, a pellet formed of a $Y_2O_3$ powder and having a diameter of 45 mm and a thickness of 2 mm was put, and a pellet formed of a $BaCuO_2$ powder and having a diameter of 45 mm and a thickness of 10 mm was further put thereon. On this, the sintered body Y—Ba—Cu—O having 6 artificial holes formed therethrough was put. Subsequently, the $Al_2O_3$-made crucible with the sintered body therein was set in an electric furnace in air, and a single crystal of $NdBa_2Cu_3O_y$ having a size of 2 mm square and a thickness of 1 mm was set as a seed at the center of the sintered body Y—Ba—Cu—O. Subsequently, this was heated up to 1100° C. in an electric furnace at a speed of 50° C./hr, then soaked as such for 1 hour, and cooled to 1050° C. taking 1 hour, and afterwards, this was gradually cooled to 950° C. at a speed of 0.2° C./hr, and then kept cooled as such in the furnace. The sample taken out of the furnace was finally annealed with oxygen in a 100% oxygen current atmosphere at 300° C. for 100 hours. In this state, the superconductive critical temperature of the sample was measured and was 90 K. Next, 6 aluminium rods each having a diameter of 1.8 mm and a length of 20 mm were inserted into the artificial holes.

The Y—Ba—Cu—O superconductive bulk magnet that had been complexed with the aluminium rods, as produced in Production Example 8, provided a trapped magnetic field of 1.0 T on the surface thereof.

Production Example 9

According to the same process of from (step 7001) to (step 7009) as in the above-mentioned Production Example 7, a superconductive bulk body of Y—Ba—Cu—O was formed. The difference from Production Example 7 is that the process herein was not followed by the step of inserting the 6 aluminium rods each having a diameter of 1.8 mm and a length of 20 mm into the artificial holes (step 7010), by the step of heating the Pb—Bi—Sn alloy at 200° C. and infiltrating it by degassing with a vacuum pump (step 7011) and by the step of arranging the Fe—Mn—Si shape-memory alloy-made ring around the bulk body, heating the Pb—Bi—Sn alloy at 300° C. and thereafter degassing the system with a vacuum pump for simultaneously attaining the pre-compression with the shape-memory alloy and vacuum infiltration (step 7012). Accordingly, in Production Example 9, aluminium rods were not inserted in the artificial rods.

In Production Example 9, in addition, a superconductive bulk body of Y—Ba—Cu—O with no artificial hole was formed. These samples were, while kept given a magnetic field of 5 T with a superconductive magnet, cooled with liquid nitrogen (77 K) for 20 minutes, and then the external magnetic field was lowered at a speed of 0.1 T/min, kept zero for 5 minutes, and thereafter the trapped magnetic field was measured using a two-dimensional scanning magnetic field distribution analyzer.

The Y—Ba—Cu—O superconductive bulk magnet not complexed with metal, as produced in Production Example 9, provided a trapped magnetic field of 0.5 T on the surface thereof.

In Production Examples 7 to 9, the same measurement was repeated. As a result, there was not recognized any significant change in these samples in point of the trapped magnetic field characteristics thereof.

In the above-mentioned Production Examples 7 to 9, the samples were cooled with a refrigerator to 50 K, but not with liquid nitrogen, and analyzed for the trapped magnetic field characteristics thereof. As a result, the Y—Ba—Cu—O superconductive bulk magnet that had been complexed with the aluminium rods and given a pre-compression load with the Fe—Mn—Si shape-memory alloy-made ring provided a trapped magnetic field of 5.0 T on the surface thereof. The Y—Ba—Cu—O superconductive bulk magnet that had been complexed with the aluminium rods provided a trapped magnetic field of 4.5 T on the surface thereof. The Y—Ba—Cu—O superconductive bulk magnet not complexed with metal provided a trapped magnetic field of 3.5 T on the surface thereof.

In the above-mentioned Production Examples 7 to 9, the same measurement was repeated. As a result, the Y—Ba—Cu—O superconductive bulk magnet that had been complexed with the aluminium rods recorded the same trapped magnetic field irrespective of the presence or absence of the Fe—Mn—Si shape-memory alloy-made ring therein. The Y—Ba—Cu—O superconductive bulk magnet not complexed with metal provided a trapped magnetic field of 3.5 T on the surface thereof.

(Experiment of Using Superconductive Bulk Magnet of Production Example 8)

Figure 14:
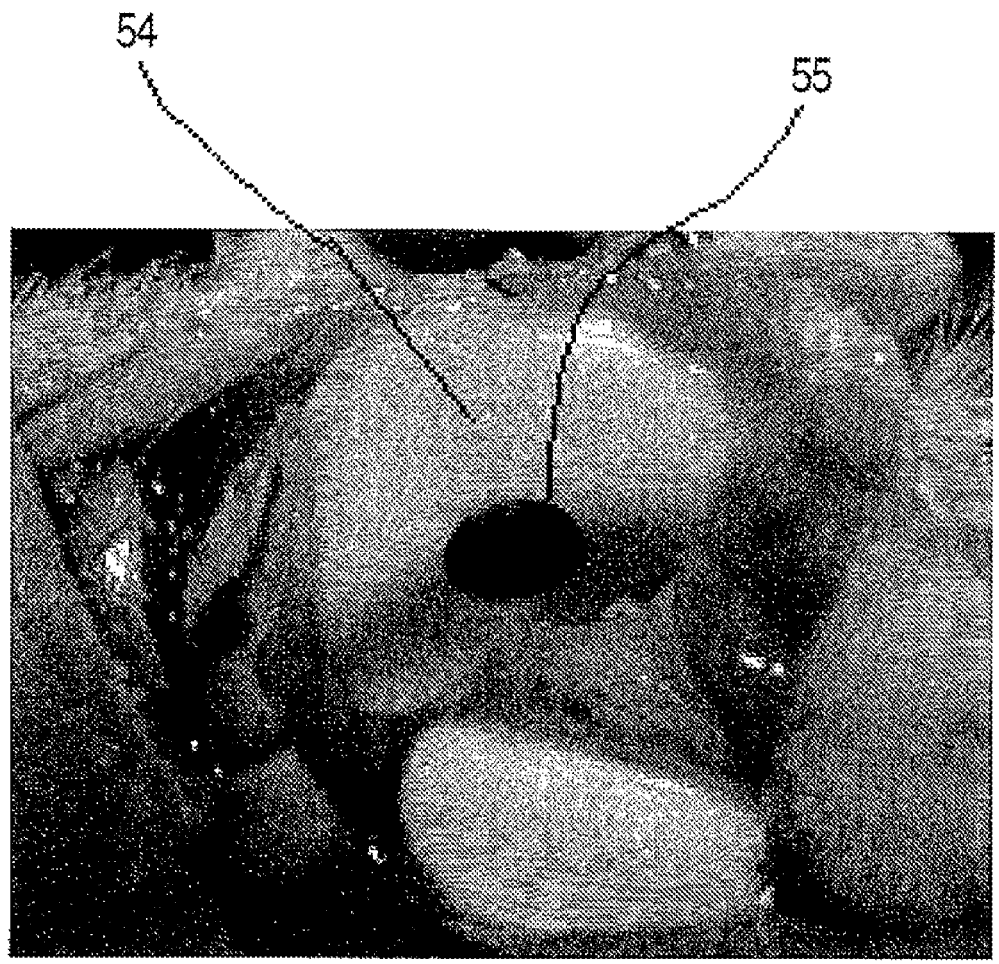
[FIG. 14] This is a picture showing the patella and the cartilage-defected part thereof of the joint part of a pig.
Figure 15:
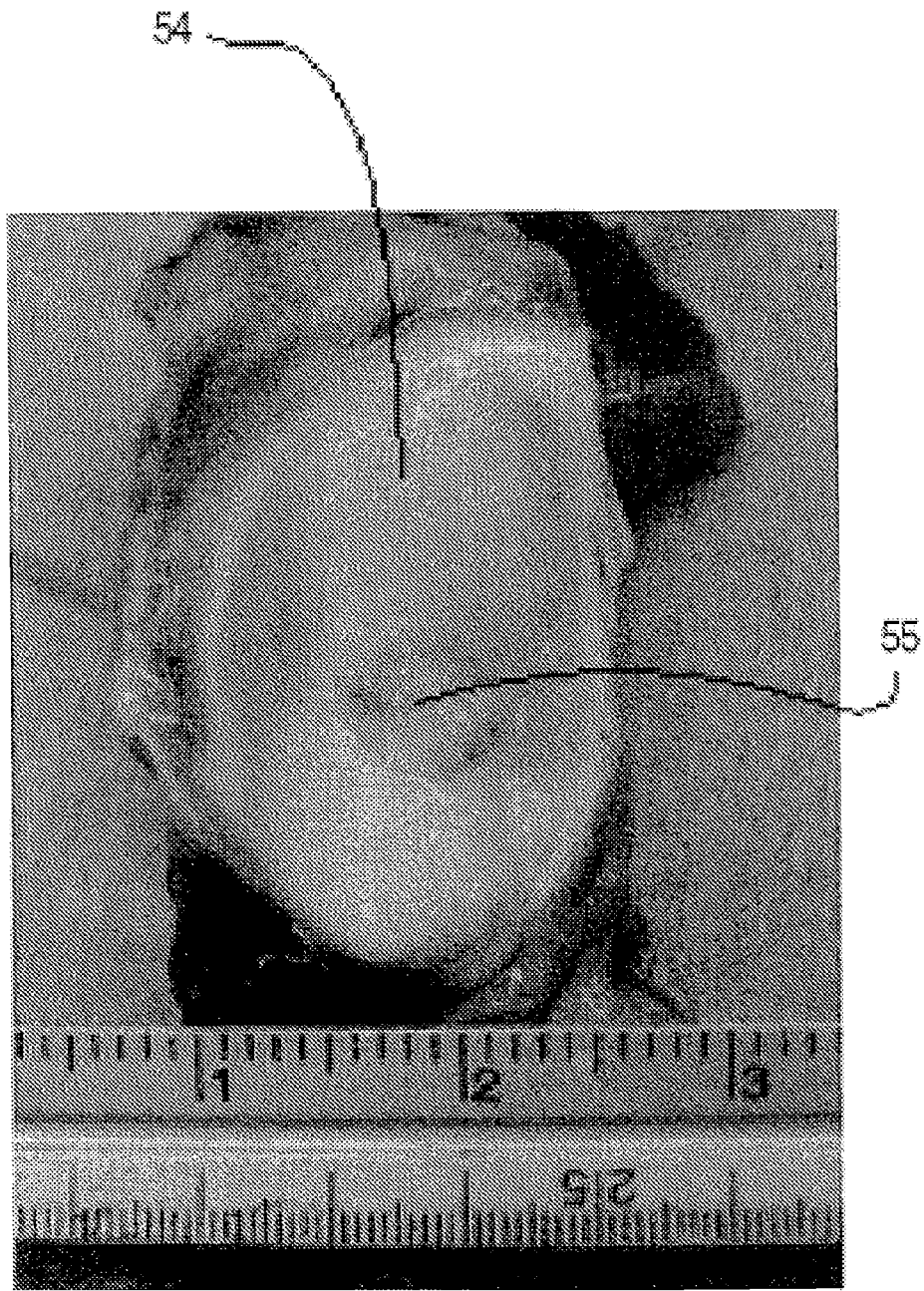
[FIG. 15] This is a picture showing the regeneration of white cartilage through self-reproduction thereof in a cartilage defected part.

FIG. 14 shows the patella of a joint part of a pig and the cartilage defected part of the bone, as obtained as a result of an animal test using the above-mentioned superconductive bulk magnet of Production Example 8. As the picture of FIG. 14 shows, a circular caved cartilage defected part 55 was physically intentionally formed in the patella 54 of a joint part of a pig, a magnetic complex formed of the stem cells of the spinal cord of a pig and magnetic beads was injected into the pig using a syringe, and while assisted by the magnetic force of a superconductive bulk magnet arranged outside the body of the pig, this was magnetically inducted to the cartilage defected part 55 and implanted therein, and thereafter the magnetic field was removed. FIG. 15 shows the picture of the cartilage defected part 55 after 3 months. As shown in FIG. 15, a white cartilage self-propagated and regenerated in the cartilage defected part 55, which confirms that the magnetic induction of the magnetic complex to the cartilage defected part 55 is effective for cartilage regeneration.

It has been known that, according to the effect, a cartilage can be uniformly regenerated in the cartilage defected part when the magnetic flux density of the magnetic field at the site of the cartilage defected part 55, as generated by the superconductive bulk magnet, is 0.8 Tesla (T) or more, or when the value of the magnetic flux density and the magnetic inclination is 1 (T2/m). The above-mentioned Examples demonstrate magnetic induction of the magnetic complex to the bone defected part of a joint; however, the invention also attains the same effect as above in any other case where the defected part is in the bone of a head, an arm or a leg owing to fracture and where the magnetic complex is magnetically inducted to the defected part.

In this, when the material mentioned below is used in producing the superconductive bulk body for the purpose of further increasing the magnetic field intensity, then the magnetic force after magnetization could be further large and the magnetic complex can be well implanted, and a large magnetic force can be made to act on deeper sites in a body from the end part of the superconductive bulk magnet 2, therefore providing the effect of favorably attaining the magnetic induction of the magnetic complex to the affected part positioned deep in the body.

The above description is made with reference to Examples; however, not limited thereto, it is obvious to anyone skilled in the art that the invention can be variously modified and changed within the sprit and the scope of the claims attached hereto.

DESCRIPTION OF REFERENCE NUMERALS

1 Magnetic Field Generation Means
2 Superconductive Bulk Magnet
3 Small-Size Refrigerator
13 Vacuum Chamber
19 Vacuum Pump
22 Power Source Unit
24 Chiller Unit
29 Superconductive Bulk Magnet Position Control Unit
30 Patient
31 Bed
33 Drive Part Housing Box
36 Rotary Drive Part
38, 40 Rotary Joint Part
42 Superconductive Bulk Magnet Holder
43 Housing Box
48 Cartilage Defected Part
50 Magnetic Complex
100 Computing Means

The invention claimed is:

1. A magnetic induction system comprising:
multiple probe-like magnetic field generation devices in which magnetic poles of magnetic field generation ends of the individual multiple probe-like magnetic field generation devices are like-poles, p1 a drive device configured to control a position and an angle of magnetic field generation end parts of the multiple magnetic field generation devices,
a computing device configured to compute the position and the angle of the magnetic field generation end parts of the magnetic field generation devices in order that a synthetic magnetic field can be formed in a desired site of a living body by the multiple magnetic field generation devices, so that the synthetic magnetic field can induct a magnetic complex to the desired site in the living body,
a drive controller configured to control the position and the angle of the magnetic field generation end parts via the drive device so that the magnetic field generation end parts of the multiple magnetic field generation devices could be in the position and at the angle computed by the computing device, and
the system further comprises a like-pole controller capable of controlling the drive device at a position at which the magnetic poles of the multiple magnetic field generation devices that do not face each other mutually repel each other at the desired site of the living body, wherein
the multiple probe-like magnetic field generation devices are arranged to work independently from each other, and
the computing device is configured to compute a route of a line of a magnetic force from a position in which the magnetic complex has been injected into the living body to the desired site by using values of the magnetic force of the multiple probe-like magnetic field generation devices and a resultant force vector of the magnetic force, and compute the position and the angle of the magnetic field generation end parts of the magnetic field generation devices necessary for the route creation.

2. The magnetic induction system as claimed in claim 1, wherein the magnetic field generation devices include a superconductive bulk magnet unit.

3. The magnetic induction system as claimed in claim 2, wherein the superconductive bulk magnet has a composition capable of providing a desired critical current density at a liquid nitrogen temperature of 77 K.

4. The magnetic induction system as claimed in claim 2, wherein the composition of the superconductive bulk magnet is RE-Ba—Cu—O, RE being a rare earth element.

5. The magnetic induction system as claimed in claim 4, wherein the composition of the superconductive bulk magnet is (Nd,Eu,Gd)—Ba—Cu—O, Gd—Ba—Cu—O or Y—Ba—Cu—O.

6. The magnetic induction system as claimed in claim 1, wherein the magnetic complex is a magnetic bead-inductee complex that comprises a magnetic bead of a magnetic material and an inductee substance.

7. The magnetic induction system as claimed in claim 1, wherein the desired site is a joint cartilage part in the living body.

8. The magnetic induction system as claimed in claim 1, further comprising a time controller for controlling the site in the living body and an intensity of the magnetic field at that site in accordance with the time elapsed after introduction of the magnetic complex, such that the intensity of the magnetic field at the site is weaker just after introduction of the magnetic complex, and is stronger after a time has elapsed from the introduction of the magnetic complex.

9. The magnetic induction system as claimed in claim 1, wherein the drive controller is provided with the function of controlling the intensity of the resultant magnetic field force of the synthetic magnetic field and a direction of a resultant magnetic field force vector by changing the relative position of the magnetic field generation end parts of the multiple magnetic field generation devices.

10. The magnetic induction system as claimed in claim 1, wherein the drive device has a rotary joint part individually connected to each of the multiple magnetic field generation devices.

11. The magnetic induction system as claimed in claim 1, wherein the multiple probe-like magnetic field generation devices include a superconductive bulk magnet and sterling type refrigerator, respectively.

12. An operating method for a magnetic induction system that comprises multiple probe-like magnetic field generation devices in which magnetic poles of magnetic field generation ends of the individual multiple probe-like magnetic field generation devices are like-poles, a drive device configured to control a position and an angle of magnetic field generation end parts of the multiple magnetic field generation devices, a computing device configured to compute the position and the angle of the magnetic field generation end parts of the magnetic field generation devices, a drive controller configured to control the drive device, and a like-pole controller,
the method comprising:
computing using the computing device the position and the angle of the magnetic field generation end parts of the magnetic field generation devices in order that a synthetic magnetic field can be formed in a desired site of a living body by the multiple magnetic field generation devices, so that the synthetic magnetic field can induct a magnetic complex to the desired site in the living body,
controlling using the drive controller the drive device so that the magnetic field generation end parts of the multiple magnetic field generation devices could be in the position and at the angle computed by the computing device, and
controlling using the like-pole controller the drive device at a position at which the magnetic poles of the multiple magnetic field generation devices that do not face each other mutually repel each other at the desired site of the living body.

13. The operating method for a magnetic induction system as claimed in claim 12, wherein:
the magnetic induction system further comprises a time controller, and
the time controller controls the site in the living body and an intensity of the magnetic field at that site in accordance with the time elapsed after introduction of a magnetic complex, such that the intensity of the magnetic field at the site is weaker just after introduction of the magnetic complex, and is stronger after a time has elapsed from the introduction of the magnetic complex.

14. The operating method for a magnetic induction system as claimed in claim 12, wherein in the step of controlling the drive device, the intensity of the resultant magnetic field force of the synthetic magnetic field is controlled by changing the relative position of the magnetic field generation end parts of the multiple magnetic field generation devices.

15. The operating method for a magnetic induction system as claimed in claim 12, wherein in the step of controlling the drive device, a direction of a resultant magnetic field force vector of the synthetic magnetic field is controlled by changing the relative position of the magnetic field generation end parts of the multiple magnetic field generation devices.

16. The operating method for a magnetic induction system as claimed in claim 12, wherein the drive device is driven by rotating a rotary joint part individually connected to each of the multiple magnetic field generation devices.

17. The operating method for a magnetic induction system as claimed in claim 12, wherein after the synthetic magnetic field is made to act in an initial area around a local part in the living body, the area in which the synthetic magnetic field is to act is narrowed to a narrow range as compared to the initial area, to thereby attain the magnetic induction to the local part.

18. The operating method for a magnetic induction system as claimed in claim 12, wherein the magnetic induction is to extravascular sites.

* * * * *